United States Patent
Lasser

(10) Patent No.: US 9,044,448 B2
(45) Date of Patent: Jun. 2, 2015

(54) X-RAY CONTRAST MEDIA COMPOSITIONS AND METHODS OF USING THE SAME

(71) Applicant: 3E THERAPEUTICS CORPORATION, La Jolla, CA (US)

(72) Inventor: Elliott C. Lasser, La Jolla, CA (US)

(73) Assignee: 3E THERAPEUTICS CORPORATION, La Jolla, CA (US)

( * ) Notice: Subject to any disclaimer, the term of this patent is extended or adjusted under 35 U.S.C. 154(b) by 0 days.

(21) Appl. No.: 13/888,256

(22) Filed: May 6, 2013

(65) Prior Publication Data

US 2014/0079810 A1 Mar. 20, 2014

Related U.S. Application Data

(63) Continuation of application No. 13/237,055, filed on Sep. 20, 2011, now abandoned.

(51) Int. Cl.
*A61K 33/30* (2006.01)
*A61K 31/192* (2006.01)
*A61K 31/196* (2006.01)

(52) U.S. Cl.
CPC ............... *A61K 33/30* (2013.01); *A61K 31/192* (2013.01); *A61K 31/196* (2013.01)

(58) Field of Classification Search
None
See application file for complete search history.

(56) References Cited

U.S. PATENT DOCUMENTS

| | | |
|---|---|---|
| 6,427,682 B1 | 8/2002 | Klimowicz et al. |
| 6,951,641 B2 | 10/2005 | Lasser |
| 7,151,117 B2 | 12/2006 | Lasser |
| 7,838,557 B2 | 11/2010 | Lasser |
| 2004/0198834 A1 | 10/2004 | Lasser |
| 2008/0275128 A1 | 11/2008 | Lasser |

FOREIGN PATENT DOCUMENTS

| | | |
|---|---|---|
| DE | 1832278 | 9/2007 |
| EP | 0363829 | 4/1990 |
| WO | 03035030 | 5/2003 |

OTHER PUBLICATIONS

Alam et al. "Strategy for effective brain drug delivery." Eur. J. Phar. Sci. 40:385-403 (201 0) (Published online May 16, 2010).
Chou et al. Distribution of antihistamines into the CSF following intranasal delivery. Dispos. 18:335-346 (1997).
Dimitriadou et al. Hydroxyzine inhibits experimental allergic encephalomyelitis (EAE) and associated brain mast cell activation. Int. J. Immunopharmacol. 22:673-684 (2000).
Malinovsky et al. Plasma concentrations of midazolam after i.v. nasal or rectal administration in children. Br. J. Anaesth. 70:617-620 (1993).
Full prescribing information for Iopamidol (Isovue 200, 250, 300, 370). Jan. 2012 revision.
Full prescribing information for Ioversol (Optiray Pharmacy Bulk Package 350, 320, 300}.Apr. 2011 revision.
Full prescribing information for Iopromide (Ul travist). Dec. 2009 revision.
Full prescribing information for Iohexol (Omnipaque 240, 300, 350), Jan. 2007 revision.
Full prescribing information for Iothalamate (Conray), Jun. 2003 revision.
Full prescribing information for Ioxaglate (Hexabrix). Feb. 2005 revision ~.
Full prescribing information for Iodipamide (Cholografin Meglumine). Jul. 2006 revision.
Full prescribing information for Iodixanol (Visipaque). May 2008 revision.
Full prescribing information for Iotrolan (Isovist). May 2008.
Full prescribing information for Diatrizoate Sodium and Meglumine (Hypaque, Sinografin, Reno-60). Jul. 2006 revision.
Full prescribing information for Azelastine Hydrochloride (Astelin). Jul. 2011 revision.
Hainfeld JF, Slatkin ON, Focella TM, Smilowitz HM. Gold nanoparticles: a new X-ray contrast agent. 2006 Br. J. Radiol. 79: 248-253.
DeCook C, Hirsh A. Anosmia due to inhalational zinc: a case report. 2000 Chem. Senses 25: 593, 659.
Bhargava et al. Ocular Allergic Disease. Drugs of Today. 34(11):957-971 (1998).
Blaug, in "Remington's Pharmaceutical Sciences" Mack publishing Company, Easton PA, 15th edition, (1975), Ch. 87.
Brasch, R. et al. "Antibodies to Radiographic Contrast Agents: Induction and Characterization of Rabbit Antibody." Invest Radiology, 2: 1-9 (1976).
Carr, D.H. and Walker, A. C. "Contrast media reactions: experimental evidence against the allergy theory." Br. J. Radiology, 57:469-473 (1984).
Ch'ng S, Wallace RA, Yuan L, et al., *Mast cells and cutaneous malignancies*. Mod Pathol: 19 (1) 149-59 (2006).
ContrastMedia_Schering document (2005), URL: http://web.archive.org/web/20050520234507/http://lhsc.uwe.ac.uk/idis2/contrast_agents/CM+Zip/ContrastMedia_Scherino.pdf).
Cousssens LM, Raymond WW, Bergers Get al., *Inflammatory mast cells up-regulate angiogenesis during squamous epithelial carcinogenesis*. Genes Dev. 13 (11): 1382-97 (1999).

(Continued)

*Primary Examiner* — Michael G Hartley
*Assistant Examiner* — Jennifer Lamberski
(74) *Attorney, Agent, or Firm* — Pillsbury Winthrop Shaw Pittman LLP

(57) ABSTRACT

Embodiments disclosed herein relate to improved X-ray contrast media compositions and methods of using the same for treating symptoms related to allergic reactions, inflammatory conditions, symptoms of the common cold and certain cancers.

7 Claims, 2 Drawing Sheets

(56) References Cited

OTHER PUBLICATIONS

Demick, 2002, URL: http://www.essortment.com/ali/typesrashesskUnnu.htm.

Dunn, C.R., Lasser, E.C. et al. "Failure to Induce Hypersensitivity Reactions to Opaque Contrast Media Analogs in guinea Pigs." Invest Radiology, 10: 317-322 (1975).

Emollient document by MedicineNet.com, URL: http://www.medicinenet.com/emollients-topical/article.htm, pp. 1-2, (2005).

Falanga V, Soter NA, Altman RD, Kerdal FA. Elevated plasma histamine levels in systemic sclerosis (Scleroderma). Arch Dermatol. Mar. 1990; 126(3):336-8.

Fingl et al, "The Pharmacological Basis of Therapeutics," Ch. 1 p. 1. (1975).

Frick, O.L. In Basic & Clinical Immunology 2nd Edition, Fudenberg, Stites, Caldwell and Wells editors; Lange Medical Publications; Chapter 22; *Immediate Hypersensitivity* (1976, 1978).

European Search Report for European Application No. 02 784 074.3 dated May 26, 2006.

Greenberger, et al. "The prevention of immediate generalized reactions to radiocontrast media in high-risk patients." The Journal of Allergy and Clinical Immunology. 87(4): 867-872 (Apr. 1991).

Hanson LR and Frey WH, "Intranasal delivery bypasses the blood-brain barrier to target therapeutic agents to the central nervous system and treat neurodegenerative disease," 2008 BMC Neuroscience, 9 (Suppl3): S3-S5)).

Ishizaka, T. et al. "Biochemical Analysis of Initial Triggering Events of IgE-Mediated Histamine Release from Human Lung Mast Cells." J Immunology, 130: 2357-62 (1983).

Katayama, H. et al. "Adverse Reactions to Ionic and Nonionic Contrast Media." *Radiology* 175: 621-628 (1990).

Kawaguchi M, Mitsuhashi Y, Kondo S. Overexpression of tumor necrosis factor-alpha-converting enzyme in psoriasis. Br J Dermatol. May 2005; 152(5): 915-9.

Krause W., et al. "Physicochemical Parameters of X-Ray Contrast Media." Invest Radiology, 29: 72-80 (1994).

Lang, J.H. and Lasser, E. C. "Binding of roentgenographic Contrast Media to Serum Albumin." Invest Radiology, 2: 396-400 (1967).

Lasser, et.al. "Pretreatment with Corticosteroids to Prevent Adverse Reactions to Nonionic Contrast Media." American Journal of Roentgenology. 162(3): 523-526 (1994).

Lasser, E. C. "The Multipotential Pseudoantigenicity of X-Ray Contrast Media." Int Arch Allergy & Immunol, 123: 282-290 (2000).

Lasser, E. C. et al. "Reports on Contrast Media Reactions: Analysis of Data from Reports to the U.S. Food and Drug Administration." Radiology 203: 605-610 (1997).

Lasser, E. C. et al. "The Significance of Protein Binding of Contrast Media in Roentgen Diagnosis." AJR. 87:338-360 (1962).

Lasser, E. C., Walters, A.J., et al. "Histamine Release by Contrast Media." Radiology, 100: 683-686 (1971).

Lasser, E.G. and Lamkin, G.E. "Can Contrast Media Act as 'Pseudoantigens'." Academic Radiology 5 (suppl. 1): S95-S98 (1998).

Lasser, et al. "A Role for Nitric Oxide in X-Ray Contrast Material Toxicity." Academic Radiology 2: 559-564 (1995).

Lasser EC and Laimkin GE. "Mechanisms of Blood Pressure Change after Bolus Injections of X-ray Contrast Media." Academic Radiology; 9 [suppl1]; S72-S75 (2002).

Lasser, Elliott C. "X-Ray Contrast Media Mechanisms in the Release of Mast Cell Contents: Understanding These Leads to a Treatment for Allergies." Journal of Allergy. vol. 2011:1-5 (2011).

Lasser et al., "Inhibition of Angiotensin-Converting Enzyme by Contrast Media: In Vitro Findings," Invest Radial1990; 25:698-702.

Leung, "Molecular Genetics and Metabolism," vol. 63, pp. 1157-1167 (1998).

Macleod et al. Immunolocalization of cytokines to mast cells in normal and allergic conjunctiva. Clin Exp Allergy. 27:1328-1334 (1997).

Maltby S, Khazaie K, McNagny KM, mast *cells in tumor growth: angiogenesis, tissue remodeling and immune modulation.* Biochem Biophys Acta. 1796(1) 19-26 (2009).

The Merck Index (Twelfth Edition 1996); title and table of contents pages provided.

Merck Manual, (2006), URL: http://www.merck.com/mmhe/sec18/ch202/ch202c.htm; accessed Jun. 5, 2010.

Myrvik, Q.N. and Weiser, R.S.—Fundamentals of Immunology, Second Edition: Lea and Febiger, Philadelphia, Chapter 7, *Interactions of Antigens and Antibodies In Vitro* (1984).

Namimatsu A. et al. "A New Method of the Measurement of Nasal Secretion in Guinea Pigs." Int Arch Allergy Appl Immunol., 95: 29-34 (1991).

"Remington's Pharmaceutical Sciences," Mack Publishing Co., Easton, PA, 18th edition, 1990; title and. table of contents pages provided.

"Remington's Pharmaceutical Sciences," Pharmaceutical Press, London, UK, 21st edition, 2011; title and table of contents pages provided.

Roitt et al. Immunology. Mosby Co, Ltd. pp. 19.1, 19.6-19.10 (1985).

Shehadi, W.H. "Adverse Reactions to Intravascularly Administered contrast Media." AJR, 124: 145-152 (1975).

Siegle, R.L. and Liebennan, P. "Measurement of Histamine, Complement components and Immune Complexes During Patient Reactions to Iodinated Contrast Material." Invest Radiology, 11:98-101 (1976).

Suto H, Nakae S, Kakurai M, Sedgwick JD, Tsai M, Galli SJ. Mast cell associated TNF promotes dendritic cell migration. J. Immunol. Apr. 1, 2006; 176(7): 4102-12.

Watanabe, N. et al. "In vitro effect of contrast agents during immunoradiometric assay for tumourassociated antigens." Nucl. Med. Commun., 19:63-70 (1998).

X-RAY CONTRAST MEDIA COMPOSITIONS AND METHODS OF USING THE SAME

BACKGROUND

1. Field

Embodiments of the technology relate to improved compositions comprising X-ray contrast media (CM) and methods of using the same to treat conditions such as allergic and inflammatory reactions.

2. Description of the Related Art

X-ray contrast media have been used for many years as radiocontrast reagents in vascular imaging using X-rays. Iodine compounds, specifically triiodinated compounds are among the commonly used X-ray contrast media used in vascular imaging.

Embodiments disclosed herein relate to improved compositions of X-ray contrast media that comprise triiodinated compounds as well as methods of using the same.

SUMMARY

Some embodiments relate to improved pharmaceutical compositions that include at least one X-ray contrast media and zinc. In some aspects, the compositions further may include a zinc chelator. In some such aspects the compositions can include a commercial X-ray contrast reagent formulation, for example, those listed herein. The chelator may include, for example, EDTA or calcium or sodium (e.g., disodium) EDTA (Ca—Na EDTA.

The zinc may be provided, for example, in an amount such that the chelator does not chelate all of the zinc. Also, the zinc may be provided, for example, in an amount such that the non-chelated zinc is in an amount sufficient to allow the zinc to associate with angiotensin converting enzyme (ACE). Where chelator is present, the amount of zinc can be for example, an amount that is sufficient to saturate the chelator that is present while leaving sufficient zinc to associate with and associate with ACE such that the ACE is active. In some embodiments described herein, the zinc can be provided in an amount, for example, of 4 milligrams (mg) to $0.1 \times 10^{-3}$ mg, or in some aspects an amount of $0.04 \times 10^{-1}$ mg-$0.1 \times 10^{-3}$ mg, in other aspects in an amount of $0.04 \times 10^{-2}$ mg-$0.1 \times 10^{-2}$ mg, or any value or sub range therein. In some aspects the amount of zinc in the aforementioned ranges can be in a 10:1 to a 1:10 ratio with the amount of chelator and/or ACE, for example. The zinc can be provided in an amount sufficient to allow zinc to act as a participant in ACE sufficient to reduce bradykinin effects.

In some aspects, the composition can be substantially free of a zinc chelator, for example, EDTA, calcium EDTA, sodium EDTA or any other form of EDTA or chelator.

The X-ray contrast media can be any satisfactory contrast media, including for example, a monomeric or dimeric, non-ionic or ionic contrast media. The X-ray contrast media can include, for example, triiodinated, completely or partially substituted, benzene moieties existing in the form of a monomer or a dimer. The X-ray contrast media can be, for example, one or more of iopamidol, ioversol, iopromide, iohexol, iothalamate (iothalamic acid), diatrizoate, ioxaglate (ioxaglic acid), iodipamide, iodixanol, iopanoic acid, sodium tyropanoate (BILOPAQUE®) and iotrolan. Other examples include acetrizoate sodium, bunamidiodyl sodium, diatrizoate sodium, iobenzamic acid, iocarmic acid, iocetamic acid, iodamide, iodophthalein sodium, ioglycamic acid, iomeglamic acid, iopental, iophenoxic acid, iopromide, ipronic acid, ioxilan, ipodate, meglumine acetrizoate, meglumine diatrizoate, metrizamide, metrizoic acid, phenobutiodil, phentetiothalein sodium, tyropanoate sodium, and combinations thereof. The amount of X-ray contrast media can be any sufficient amount to treat the specific indication as listed herein. In some non limiting aspects, the X-ray contrast media (CM) can be provided in a concentration, for example, of 150 Mg I/mL to 350 Mg I/mL. In some aspects the amount or dosage of administered CM can be, for example, from about 0.001 grams to about 200 grams, depending up on the location of delivery and the condition being treated, for example.

Some embodiments relate to methods of treating one or more of an allergic reaction, an inflammatory reaction, the symptoms of a common cold (including for example those that are not adequately treating by antihistamine or other medications), or a cancer (e.g., thyroid) in a mammal in need thereof, comprising providing or administering a composition as described above or elsewhere herein to the mammal in an amount sufficient to treat the particular condition.

Still some embodiments relate to methods of treating an allergic reaction or an inflammatory reaction in a mammal in need thereof, comprising providing a composition comprising one or more X-ray contrast media to a mammal that has an allergic reaction or an inflammatory reaction. In some aspects the composition can be substantially free of a zinc chelator and/or the composition can include an amount of zinc, for example, an amount sufficient to act in concert with angiotensin converting enzyme (ACE). In some aspects the amount of zinc can be, for example, from $0.04 \times 10^{-2}$ mg to $0.1 \times 10^{-2}$ mg. The methods further may include, for example, contacting at least part of the tissue of the mammal with a therapeutically effective amount of the composition that includes the X-ray contrast media, wherein the contacting is to a part of the tissue associated with the allergic reaction or inflammatory reaction.

The zinc chelator can be, for example, Ca-EDTA, Na-EDTA or EDTA. In some aspects the composition may be or include, for example, less than 10 milli-molar or even less than 10 micro molar zinc chelator. Substantially free of zinc chelator can mean, for example, that the composition includes about 0.0001% to about 5% chelator or any value there between.

The allergic condition can be, for example, one or more of, allergic rhinitis or allergic conjunctivitis. In some aspects the allergic condition can be, for example, one or more of asthma, insect venom allergy, food allergy, a drug allergy, a latex allergy, a cosmetic allergy, a perfume allergy, a cleanser allergy, a metal allergy and the like.

The methods further may include, for example, identifying the mammal as being a mammal suffering from a symptom associated with bradykinin activity. In some aspects the mammal can be identified as having increased immune cell activity, increased nasal airway resistance, increased congestion, etc. The methods further can include, for example, identifying the mammal as a mammal that suffers from a condition related to skin inflammation or dermatitis. For example, the condition can be one or more of eczema, dermatosis, insect bite reaction, sunburn, other skin allergen reactions, and the like. The skin allergen reaction can be, for example, a reaction resulting from a vaccine, a reaction resulting from a sensitizing antigen, and the like. The skin allergen can be, for example, poison ivy, poison oak, poison sumac, a cleaning solution (including shampoo), a detergent, a cosmetic, a perfume, an industrial chemical, a latex rubber, a dust allergen, a grass allergen, and the like. The dermatosis can be, for example, psoriasis.

In some embodiments, the composition may be formulated, for example, as a topical formulation. The topical formulation may include, for example, a formulation such as a gel formulation, a cream formulation, a lotion formulation, a paste formulation, an ointment formulation, an oil formulation, and a foam formulation. The composition further may include, for example, an absorption emollient.

In some embodiments, at least part of the affected area of the mammal is contacted with the composition on a daily basis, on an as-needed basis, or on a regular interval such as twice daily, three times daily, every other day, etc. The composition can be administered for a period of time ranging from a single as needed administration to administration for 1 day to multiple years, or any value there between, (e.g., 1-90 days, 1-60 days, 1-30 days, etc.). The dosages described herein can be daily dosages or the dosage of an individual administration, for example, even if multiple administrations occur (e.g., 2 sprays into a nostril).

The X-ray contrast media can include, for example, either a monomeric or dimeric, nonionic or ionic contrast media. The X-ray contrast media may include, for example, a triiodinated, completely or partially substituted, benzene moieties existing in the form of a monomer or a dimer. The X-ray contrast media can include, for example, one or more of iopamidol, ioversol, iopromide, iohexol, iothalamate (iothalamic acid), diatrizoate, ioxaglate (ioxaglic acid), iodipamide, iodixanol, iopanoic acid, sodium tyropanoate (BILOPAQUE®) and iotrolan. Other examples include acetrizoate sodium, bunamidiodyl sodium, diatrizoate sodium, iobenzamic acid, iocarmic acid, iocetamic acid, iodamide, iodophthalein sodium, ioglycamic acid, iomeglamic acid, iopental, iophenoxic acid, iopromide, ipronic acid, ioxilan, ipodate, meglumine acetrizoate, meglumine diatrizoate, metrizamide, metrizoic acid, phenobutiodil, phentetiothalein sodium, tyropanoate sodium, and combinations thereof.

Some embodiments relate to methods of treating inflammation of the upper respiratory track/bronchi in a mammal in need thereof, for example, by contacting at least part of the upper respiratory tract/bronchi of a mammal with a therapeutically effective amount of a composition as described above or elsewhere herein. In some aspects the methods can include providing or administering a composition that is substantially free of zinc chelator and/or includes a sufficient amount of zinc as described herein. The methods further can include identifying the mammal as a mammal that suffers from a condition related to inflammation of the upper respiratory track/bronchi. The composition can be, for example, formulated as an aerosol formulation, including formulated for use in a nebulizer or an inhaler. The composition further may include, for example, a preservative.

Also, some embodiments relate to methods of treating a colon inflammatory condition in a mammal in need thereof. The methods can include, for example, contacting at least part of the colon of a mammal with a therapeutically effective amount of a composition as described above or elsewhere herein. In some embodiments the methods can include providing or administering a composition that comprises a sufficient amount of an X-ray contrast media where the composition is substantially free of zinc chelator and/or includes an amount of zinc as described herein. The methods further can include, for example, identifying the mammal as a mammal who suffers from a colon inflammatory condition. The condition can be, for example, inflammatory bowel disease, irritable bowel syndrome, and the like. The composition can be formulated, for example, as a retention enema.

Some embodiments relate to methods of treating a condition related to inflammation of the esophagus in a mammal in need thereof. The methods can include, for example, contacting at least part of the esophagus of the mammal with a therapeutically effective amount of a composition as described above and elsewhere herein. In some embodiments the methods can include providing or administering a composition that comprises a sufficient amount of an X-ray contrast media where the composition is substantially free of zinc chelator and/or includes an amount of zinc as described herein. The methods further may include, for example, identifying the mammal as a mammal who suffers from a condition related inflammation of the esophagus. The condition can be, for example, allergic esophagitis.

Still some embodiments relate to methods of treating a cancer (e.g., of the thyroid) in a mammal in need thereof. The methods can include, for example, contacting, providing or administering a therapeutically effective amount of a composition as described herein to a mammal in need thereof. For example, in the non-limiting example of cancer of the thyroid, the methods can include injecting intravascularly the mammal with a therapeutically effective amount of a composition that will be taken up by the thyroid and in which the CM iodides may or may not be made radioactive. The methods further can include, for example, identifying the mammal as a mammal who suffers from a cancer, such as for example, a cancer of the thyroid.

Further embodiments relate to methods of treating a common cold. The methods can include, for example, contacting, providing or administering a therapeutically effective amount of a composition as described herein with a mammal in need thereof. The methods further may include identifying the mammal as a mammal suffering from a common cold. In some aspects, the treating the common cold can include, for example, treating a symptom of the common cold.

Some embodiments relate to methods of treating a nasal allergic condition in a mammal in need thereof. The methods can include, for example, providing or administering to a nasal tissue of a mammal suffering from a nasal allergic condition a composition that includes an X-ray contrast media in an amount sufficient to treat said nasal allergic condition, wherein the composition is at least substantially free of a zinc chelator and/or includes a sufficient amount of zinc to reduce the inhibition of angiotensin converting enzyme (ACE). The nasal allergic condition can be, for example, allergic rhinitis.

The zinc chelator can be, for example, one or more of Ca-EDTA, Na-EDTA, EDTA or any other chelator. In some aspects, the term substantially free can mean that the compositions include less than 10% or less than 5% zinc chelator. In some aspects the composition can be free of the chelator, for example, Ca-EDTA, Na-EDTA, EDTA and the like.

The compositions can include, for example, zinc in amount sufficient to act in concert with angiotensin converting enzyme (ACE). In some aspects, the amount of zinc can be from $0.04 \times 10^{-1}$ mg to $0.1 \times 10^{-3}$ mg for dosage.

The X-ray contrast media can be or can include, for example, a monomeric or dimeric, nonionic or ionic contrast media. The X-ray contrast media may include, for example, one ore more triiodinated, completely or partially substituted, benzene moieties existing in the form of a monomer or a dimer. The X-ray contrast media can include or be one or more of iopamidol, ioversol, iopromide, iohexol, iothalamate (iothalamic acid), diatrizoate, ioxaglate (ioxaglic acid), iodipamide, iodixanol, iopanoic acid, sodium tyropanoate (BILOPAQUE®) and iotrolan. Other examples include acetrizoate sodium, bunamidiodyl sodium, diatrizoate sodium, iobenzamic acid, iocarmic acid, iocetamic acid, iodamide, iodophthalein sodium, ioglycamic acid, iomeglamic acid, iopental, iophenoxic acid, iopromide, ipronic acid, ioxilan, ipodate, meglumine acetrizoate, meglumine diatrizoate, metrizamide, metrizoic acid, phenobutiodil, phentetiothalein sodium, tyropanoate sodium, combinations thereof, and the like. In some aspects, the X-ray contrast media can include or be, one or more of iopamidol, ioversol, iopromide, iohexol, iothalamate (iothalamic acid), diatrizoate, ioxaglate and combinations thereof. In some non limiting aspects the X-ray contrast media may be provided or administered in an amount of 150 mg I/mL to 350 mg I/mL.

Some embodiments relate to topical compositions that include a composition as described above and elsewhere herein and a pharmaceutically acceptable topical carrier. The topical compositions may be, for example, formulated as a formulation selected from a gel, a cream, a lotion, a paste, an ointment, an oil, a foam, and the like. The composition may be, for example, formulated to be substantially absorbed by an epidermal layer of the skin. The pharmaceutically acceptable carrier can include, for example, an absorption emollient.

Other embodiments relate to aerosol compositions that include, for example, a composition as described herein and an aerosolized pharmaceutically acceptable carrier solution or dry powder. The compositions may be formulated, for example, to be substantially absorbed by a bronchus. The compositions also may include, for example, one or more of dichlorodifluoromethane, trichlorofluoromethane, dichlorotetrafluoroethane, carbon dioxide, and the like. The compositions can be formulated for use in a nebulizer or an inhaler, for example.

It should be noted that some embodiments relate to compositions and methods of using the compositions, where the compositions include one or more allergy medications, for example, an antihistamine and where the composition is either free or substantially free of zinc chelator and/or includes zinc. The term substantially free can mean that the composition includes from 0.5% to 10% chelator, less than 5% chelator, less than 4%, 3%, 2% or 1% chelator, for example. Any allergy indication can be treated, including those described herein. For example, the compositions can be used to treat allergic rhinitis or conjunctivitis for example.

The addition of zinc and/or the removal of chelator can provide the added benefit of for treating allergic symptoms. For example, in the context of conjunctivitis, the compositions can be effective at relieving not only nasal itch, secretions and sneezing, but also can provide benefit for nasal congestion, which often is not adequately treated with anti allergy medications. The amount of zinc can be any amount as described herein. In some aspects the amount of zinc can be an amount that partially, substantially or completely saturates the zinc chelator and leaves sufficient zinc to interact with ACE in order to permit ACE to act in its enzymatic capacity. As used in such embodiments, the term substantially in the context of the amount of zinc can mean that the amount of zinc saturates at least 50%, at least 60%, at least 70%, at least 80%, at least 90%, at least 95%, at least 96%, 97%, 98% or at least 99% of the chelator, for example. Some non-limiting examples of allergy medications that can be used in such embodiments include liquid antihistamines and "mast cell stabilizers." Some specific examples of medications that can be formulated as described herein to include added zinc or to be free or substantially free of chelator include, without limitation, Olopatadine, Ceterizine, Loratadine, Ketofin, Diphenhydramine, and the like. In some aspects the compositions further may include a CM in an amount as described herein and/or in a composition as described herein, for example. Some embodiments relate to methods where the allergic medication compositions as described in this paragraph and elsewhere herein are used in a combination therapy with one or more of the CM compositions described herein where the combination products are administered together or separate, at the same time (together or separately) or at different times, for example.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and therefore, are not to be considered limiting of its scope, the disclosure will be described with additional specificity and detail through use of the accompanying drawings.

DETAILED DESCRIPTION OF THE PREFERRED EMBODIMENT

Figure 1:
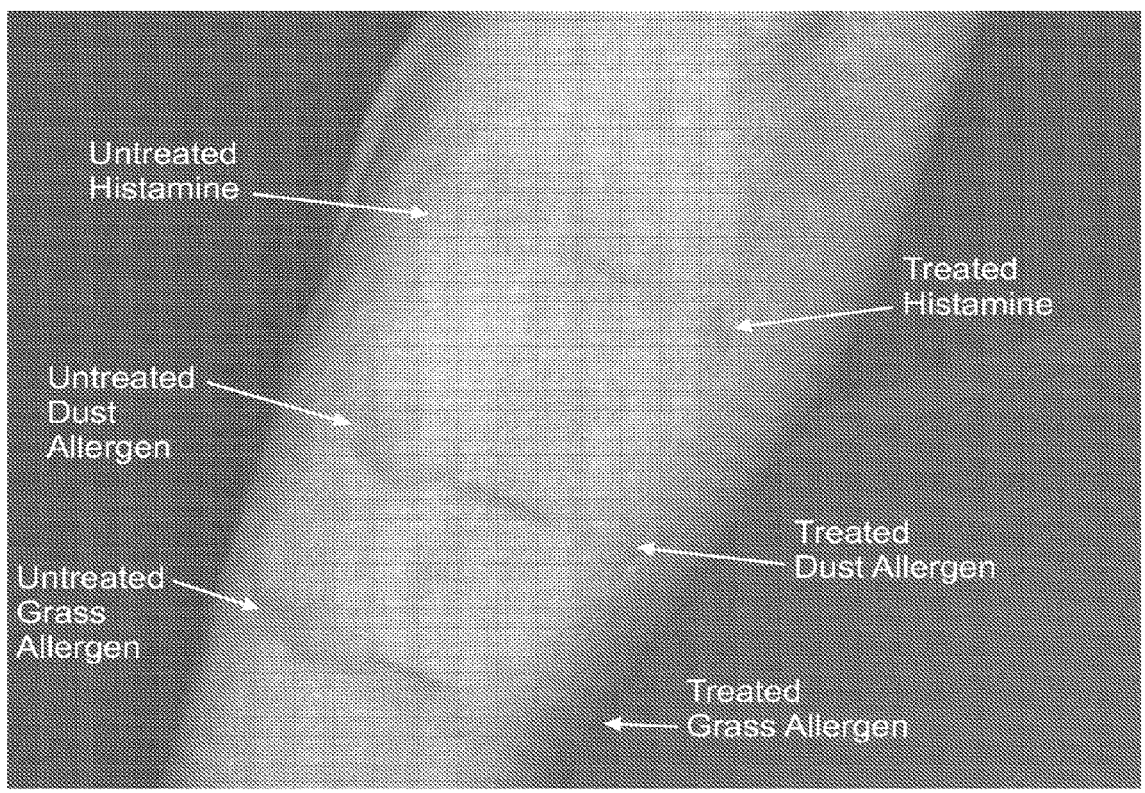
FIG. 1 is a photograph showing the response of a patient to 6 injections of allergens (2×3 different allergens) where the response to each allergen is shown with and without CM treatment.

The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Embodiments disclosed herein generally relate to the surprising and unexpected discovery of improved methods of treating various conditions and compositions for the treatment of those various conditions. More specifically embodiments generally relate to improved compositions comprising X-ray contrast media (CM) (and/or other allergy medications as described herein) and methods of using the same to treat various conditions as described herein such as, for example, allergic and inflammatory conditions.

The inventor has previously shown that certain CM can be used to treat allergic reactions. See for example, U.S. Pat. No. 7,838,557, which is incorporated herein by reference in its entirety. Through both basic studies and clinical studies the inventor has discovered that CM have the unique potential to inhibit antigen-antibody reactions. While a sufficient concentration of CM for inhibiting antigen-antibody reactions can be difficult to attain on intravascular injection of CM, the inventor has discovered that it can be easily attained on topical administration. Without being limited thereto, the inventor concluded that the CM must bind to the Fc portion of the IgE molecules, and at a sufficient concentration, the CM supply enough bulk to prevent the bridging and consequent aggregation of adjacent IgE molecule receptors necessary to initiate mast cell discharge.

Some embodiments herein are based at least in part upon studies using commercially available CM provided by their respective manufacturers. For example, a 20 patient study was conducted utilizing the commercially available CM, HEXABRIX® (ioxoglate), in patients with induced allergic rhinitis. Disturbingly and unexpectedly, the results showed that while the CM produced substantial reductions in the incidence of sneezing and runny nose, stuffy nose and itching did not reach significance, and measured nasal airway resistance (NAR) did not differ from placebo.

The CM used in the study was provided in its standard glass vial at a concentration for intravascular use. The CM compositions included either ethylenediaminetetraacetate (EDTA), Ca-EDTA or Na-EDTA (which are referred to herein as well as EDTA or Ca—Na EDTA), which for many years CM manufacturers have included in the glass vials containing the CM compositions. The EDTA and Ca—NA EDTA were included by the manufacturers in order to chelate any substances that might be leached off of the glass vials. Neither substance has any obvious effect when the CM are used for vascular imaging. Even at the vial concentrations, the topical administration of CM in the small amounts for topical allergic reactions provided the patients with only about 1/250 of the doses of CM commonly administered intravascularly. However, the inventor has now discovered that the doses provided enough Ca—Na EDTA or EDTA to adversely impact the treatment of the symptoms of conditions such as, for example, the conditions of allergic and inflammatory reactions.

As a result of research and studies, the inventor has surprisingly and unexpectedly discovered that commercially available CM compositions that include the EDTA/Ca—Na EDTA adversely impact complete resolution of various medical conditions or reactions, including for example, allergic reaction reactions and inflammatory reactions as described herein. Without being limited thereto, it is believed that the CM compositions result in the less than optimal resolution due to the EDTA/Ca—Na EDTA chelating zinc. Zinc is a required metal enzyme for angiotensin converting enzyme (ACE).

Figure 2:
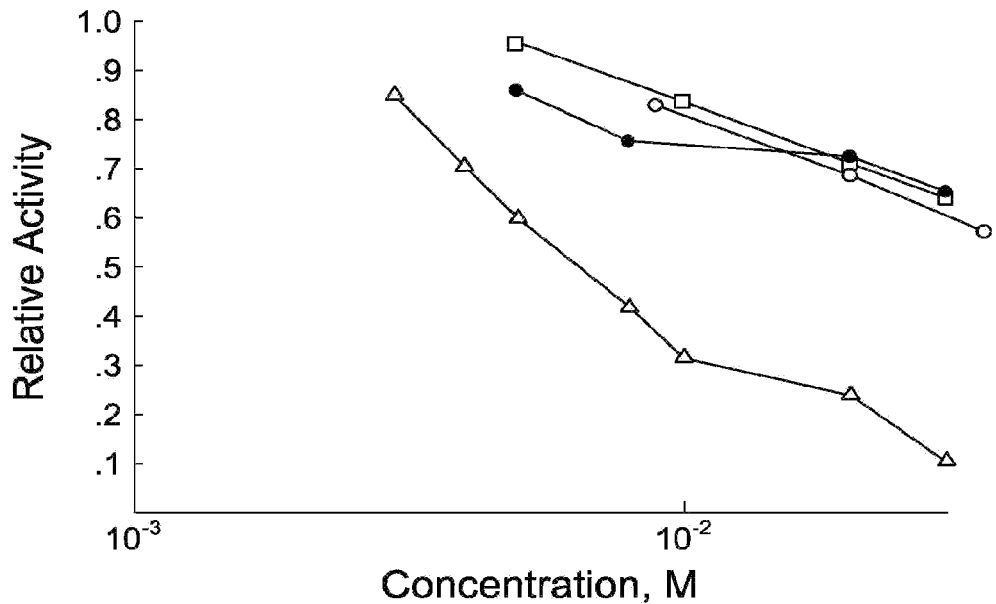
FIG. 2 is a graph showing the relative activity (inhibition) of angiotensin converting enzyme (ACE) in a purified contrast media (contains no chelator), the commercial contrast media (contains Ca—Na ethylenediaminetetraacetate (EDTA)), the commercial media with sufficient zinc sulfate added to neutralize the chelator. The inhibition of ACE by purified iopamidol, commercial iopamidol (contains chelator), and iopamidol with sufficient zinc sulfate added to neutralize the chelator is shown. Also shown is the calculated inhibition for commercial iopamidol when the inhibition contributed by the chelator has been subtracted. Removing the chelator or neutralizing its effect by adding zinc diminishes the inhibition ACE significantly. Open triangle (Δ–Δ): commercial iopamidol; Open circle (○–○): purified iopamidol; open square (□–□) commercial iopamidol plus zinc; and closed circle (●–●): calculated iopamidol-chelator. See, Laser et al., "Inhibition of Angiotensin-Converting Enzyme by Contrast Media: In Vitro Findings," Invest Radial 1990; 25:698-702, which is incorporated herein by reference in its entirety.

The inventor previously studied the potential inhibition of ACE by contrast media in vitro in the context of intravascular/systemic use of CM (Laser et al., "Inhibition of Angiotensin-Converting Enzyme by Contrast Media: In Vitro Findings," Invest Radial 1990; 25:698-702, which is incorporated herein by reference in its entirety). ACE inhibition in the context of intravascular radiologic use is likely of little consequence since the dilution of the CM when administered into the vascular system dilutes the EDTA to the point where the amount reaching any distal tissue would be inconsequential. FIG. 2 which is reproduced from that paper shows the relative activity (inhibition) of angiotensin converting enzyme (ACE) in a purified contrast media (contains no chelator), the commercial contrast media (contains Ca—Na ethylenediaminetetraacetate (EDTA)), and the commercial media with sufficient zinc sulfate added to neutralize the chelator. The removal of chelator or the addition of zinc resulted in increased ACE activity. The role of ACE inhibition in allergic and inflammatory reactions, particularly when treating such conditions with CM was not previously appreciated or explored. However, in the context of treating allergic reactions or inflammatory reactions as described herein for example, the inventor has surprisingly and unexpectedly discovered that ACE inhibition appears to impact the resolution and treatment of symptoms, including surprisingly, symptoms that previously were not adequately alleviated by CM or other medications.

ACE is the major enzyme involved in the break down of bradykinin to its ineffective metabolites. When zinc is chelated by EDTA or Ca—Na EDTA, ACE is inhibited and bradykinin is not broken down. If ACE does not efficiently breakdown bradykinin, the bradykinin, along with histamine and nitric oxide, can result in more severe allergic and inflammatory reactions. The failure to enzymatically breakdown bradykinin into its metabolites can have another important effect. It produces an increase of nasal airways resistance (NAR) that is greater than the resistance produced by histamine in both magnitude and duration. This accounts for the relative lack of efficiency of H1 antihistamines to have an effect on nasal blockage in allergic rhinitis. Some embodiments described herein are based upon that discovery and that removing the EDTA/Ca—Na EDTA from CM compositions and/or adding sufficient zinc to the compositions can reduce or avoid the inhibition of ACE, which can result in improved treatment of allergic and inflammatory reactions.

Some embodiments described herein are based upon the surprising and unexpected discovery of improved CM compositions and their use to treat various conditions. Specifically, stuffy nose, itching and/or NAR can be improved by removing some or all of the Ca—Na EDTA or EDTA from the compositions. Also, CM compositions can be improved by adding an amount of zinc to the compositions such that enough zinc remains available (notwithstanding the EDTA/Ca—Na EDTA) to act as an ACE enzyme. The zinc can be added to compositions that include or don't include the EDTA (or Ca-EDTA). Removal of the EDTA/Ca—Na EDTA and/or the addition of a sufficient amount of zinc can improve the compositions for use in the treatment of allergic reactions, particularly topically treated allergic reactions. The improved composition also can be used to treat inflammatory conditions and other conditions as described herein.

X-Ray Contrast Media (CM)

As already noted, X-ray contrast media (CM) have been used for many years in the field of radiology. While the molecules have assumed some structural differences over the years, the basic concept that iodine attached to organic ring structures will impair X-ray penetration remains the same.

The X-ray molecules, referred to as "contrast media" have been used to opacify blood vessels, organs, and other parts of the body that have orifices leading externally or are amenable to needle injection.

X-ray contrast media today are generally triiodinated, completely or incompletely substituted, benzene moieties existing in the form of a monomer or a dimer. The following illustrates the general structure of CM monomers:

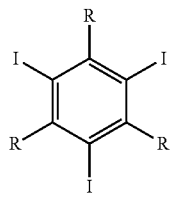

The following illustrates the general structure of CM dimers:

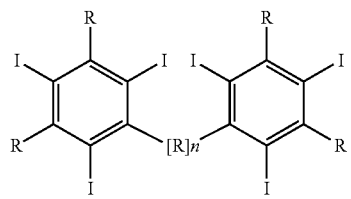

In the above depicted monomer and dimer, each R separately may represent any of a variety of substituents and n may represent any number of units ranging from 1 to 10. For example, without being limited thereto, each respective R separately may include a hydrogen, a halogen, a mono-substituted, a poly-substituted or an unsubstituted variant of the following residues: saturated $C_1$-$C_{24}$ alkyl, unsaturated $C_2$-$C_{24}$ alkenyl or $C_2$-$C_{24}$ alkynyl, acyl, acyloxy, alkyloxycarbonyloxy, aryloxycarbonyloxy, cycloalkyl (including for example, cyclohexylcarbinol), cycloalkenyl, alkoxy, cycloalkoxy, aryl, heteroaryl, arylalkoxy carbonyl, alkoxy carbonylacyl, amino, aminocarbonyl, aminocarboyloxy, nitro, azido, phenyl, cycloalkylacyl, hydroxy, alkylthio, arylthio, oxysulfonyl, carboxy, cyano, thio, sulfoxide, sulfone, sulfonate esters, thiocyano, boronic acids and esters, and halogenated alkyl including polyhalogenated alkyl.

These contrast media molecules can be either ionic or nonionic (or in the case of one dimer, part ionic and part nonionic). They can be monomeric or dimeric, for example. Generally, there can be slight variations in the amide side chains attached at the 3 and 5 positions on the ring and in the nature of the cations (for the ionic media) and there can be slight differences in the length of the aliphatic chains linking the dimers and in the nature of the coupler group. In some aspects the CM can be triiodinated. In some aspects the CM can be completely or partially substituted benzene moieties. In some aspects the CM can be triiodinated, completely or partially substituted, benzene moieties existing in the form of a monomer or a dimer, for example.

Some examples of X-ray contrast media that are commercially available today are iopamidol, ioversol, iopromide, and iohexol which are nonionic monomers. Iothalamate and diatrizoate are ionic monomers. Ioxoglate and iodipamide are ionic dimers, while iodixanol and iotrolan are nonionic dimers. Any X-ray contrast media can be used in the methods and compositions described herein, including for example, iopamidol, ioversol, iopromide, iohexol, iothalamate (iothalamic acid), diatrizoate, ioxaglate (ioxaglic acid), iodipamide, iodixanol, iopanoic acid, sodium tyropanoate (BILO-PAQUE®) and iotrolan. Other examples include acetrizoate sodium, bunamidiodyl sodium, diatrizoate sodium, iobenzamic acid, iocarmic acid, iocetamic acid, iodamide, iodophthalein sodium, ioglycamic acid, iomeglamic acid, iopental, iophenoxic acid, iopromide, ipronic acid, ioxilan, ipodate, meglumine acetrizoate, meglumine diatrizoate, metrizamide, metrizoic acid, phenobutiodil, phentetiothalein sodium, tyropanoate sodium, and the like. The formulas and structures of the above-listed CM can be found in a variety of sources, including for example The Merck Index (Twelfth Edition 1996), which is incorporated herein by reference in its entirety. Any one or more of the contrast media described herein can be specifically excluded from the methods and compositions described herein.

Compositions

Some embodiments relate to compositions comprising one or more CM, including one or more of the CM listed herein. In particular, some embodiments relate to compositions comprising one or more CM and an amount of zinc. In some aspects, a commercial CM formulation comprising any of the compounds listed above can be used with the addition of a sufficient amount of zinc. For example, the commercial CM, without being limited thereto, can be one or more of HEXABRIX®, CONRAY®, ISOVIST™, OPTIRAY®, CHOLOGRAFIN®, ISOVUE®, ANGIOVIST™. Some embodiments relate to compositions comprising one or more CM in a composition that is free of a chelator, for example, a zinc chelator such as Ca—Na EDTA or EDTA. Some embodiments relate to compositions comprising one or more CM, an amount of zinc and/or a reduced amount of a chelator or no chelator. When a reduced amount of chelator is present, then the amount of zinc can be an amount sufficient to have an excess amount of non-chelated zinc to enable ACE to exert its enzymatic function, for example, in order to break down bradykinin.

In some embodiments, one or more of the compounds described or listed herein can be specifically excluded. For example, without being limited thereto, in some aspects one or more of ioxaglate, iopamidol, iotrolan or iodixanol can be specifically excluded from the compositions.

By avoiding or reducing the chelator, such as the Ca-EDTA, Na-EDTA (Ca—Na EDTA or CaNA-EDTA can refer to each individually or both collectively herein) and EDTA, the compositions can avoid, reduce or minimize inhibition of ACE. Likewise, the addition of zinc to compositions that include a chelator can avoid inhibition of ACE due to the presence of additional zinc, which zinc remains available for interaction with ACE.

As noted above, some embodiments relate to compositions that include an anti allergy medication, for example an antihistamine, that is not a CM (although the compositions can further include or be used with CM or CM compositions), where the compositions are free or substantially free of chelator and/or include zinc. The term substantially free can mean that the composition includes from 0.5% to 10% chelator, less than 5% chelator, less than 4%, 3%, 2% or 1% chelator, for example. Any allergy indication can be treated, including any of those described herein. Other conditions described herein that might utilize and anti allergy medication such as an antihistamine can also utilize the improved allergy medication compositions described in this paragraph and elsewhere herein. For example, the compositions can be used to treat allergic rhinitis or conjunctivitis. The addition of zinc and/or the removal of chelator can provide the added benefit of for treating allergic symptoms. For example, in the context of conjunctivitis, the compositions can be effective at relieving not only nasal itch, secretions and sneezing, but also can provide benefit for nasal congestion, which often is not adequately treated with anti allergy medications. The amount of zinc can be any amount as described herein. In some aspects the amount of zinc can be an amount that partially, substantially or completely saturates the zinc chelator and leaves sufficient zinc to interact with ACE in order to permit ACE to act in its enzymatic capacity. As used in such embodiments, the term substantially in the context of the amount of zinc can mean that the amount of zinc saturates at least 50%, at least 60%, at least 70%, at least 80%, at least 90%, at least 95%, at least 96%, 97%, 98% or at least 99% of the chelator, for example. Some non-limiting examples of allergy medications that can be used in such embodiments include liquid antihistamines and "mast cell stabilizers." Some specific examples of medications that can be formulated as described herein to include added zinc or to be free or substantially free of chelator include, without limitation, Olopatadine, Ceterizine, Loratadine, Ketofin, Diphenhydramine, and the like. In some aspects the compositions further may include a CM in an amount as described herein and/or in a composition as described herein, for example. Some embodiments relate to methods where the allergic medication compositions as described in this paragraph and elsewhere herein are used in a combination therapy with one or more of the CM compositions described herein where the combination products are administered together or separate, at the same time (together or separately) or at different times, for example.

The chelator compound can be for example, Ca-EDTA, Na-EDTA, EDTA or any other chelator, in particular a chelator that chelates zinc. In compositions that do not include a zinc chelator, for example, the amount of zinc can be any amount that is sufficient to reduce or avoid ACE inhibition. For example, the concentration of zinc can be from about $3 \times 10^{-3}$ M to about 3.0 M or any sub-range of value there between (e.g., $3 \times 10^{-2}$ M to about $3 \times 10^{-1}$ M), or any other amount described herein. Similarly, where there is a chelator in the composition, the amount of zinc can be an amount sufficient to produce enough non-chelated zinc to avoid ACE inhibition. For example, the concentration can be from about 3.0 M to about $2 \times 10^{-4}$ M or any sub-range of value there between ($3 \times 10^{-2}$ M to about $2 \times 10^{-3}$ M), or any other amount described herein. In some embodiments, described herein, the zinc can be provided in an dosage (e.g., individual dosage or total daily), for example, of 4 mg-$0.1 \times 10^{-3}$ mg, or in some aspects an amount of $0.04 \times 10^{-1}$ mg-$0.1 \times 10^{-3}$ mg, in other aspects in an amount of $0.04 \times 10^{-2}$ mg-$0.1 \times 10^{-2}$ mg, or any value or sub range therein. In some aspects the amount of zinc in the aforementioned ranges can be in a 10:1 to a 1:10 ratio with the amount of chelator and/or ACE, for example. The zinc can be provided in an amount sufficient to allow zinc to act as a participant in ACE sufficient to reduce bradykinin symptoms In some embodiments, the amount of zinc can be limited to avoid potential adverse effects associated with zinc. For example, the use of zinc in certain products, such as ZICAM®, reportedly caused anosmia—the loss of the sense of smell—as a result of using the product, which consisted of a zinc gluconate gel. Accordingly, in some embodiments the amount zinc can be in an amount less than the amount found in the ZICAM® nasal gel product or an amount that does not produce or result in anosmia. For example, the amount can be an amount that is less than 10 milli molar or less than 10 micro molar, for example.

The compositions further can include other excipients, carriers and materials as detailed more fully below.

Methods of Use

Allergic Reactions:

Some embodiments relate to methods of treating a patient suffering from or at risk of suffering from an allergic reaction, including in some aspects allergic reactions characterized by increased NAR that is not fully responsive to antihistamine treatment. In some aspects the allergic reaction can be local or systemic. In some aspects the allergic reaction can be anaphylactic.

For example, the allergic reaction can be allergic rhinitis, allergic conjunctivitis, asthma, insect venom allergy, food allergy, a drug allergy, a latex allergy, a cosmetic allergy, a perfume allergy, a cleanser allergy, a metal allergy, and the like. The allergy can be treated by topical administration of a composition as described herein. In some embodiments the methods can include identifying a patient with increased NAR and/or NAR that is not satisfactorily treated for NAR. In some embodiments, the CM compositions used to treat the allergic reaction can include one or more of the CM described herein. In some aspects of the embodiments, one or more of the contrast media described herein can be excluded. In some embodiments, any one of the specific indications described below can be specifically excluded.

Some embodiments relate to combination therapies utilizing CM compositions and methods as described herein. For example, the CM compositions can be used (e.g., administered together or separately) in combination with other allergy treatments such as with antihistamines, decongestants, steroids, anti-inflammatory products, etc.

As one non-limiting example, the CM compositions can be used in combination with nasal allergy medications in order to treat allergic rhinitis (also reactions of the nasal passage associated with the common cold or nasal inflammatory reactions). Non-limiting examples of nasal allergy medications include nasal sprays such as steroidal beclomethasone BECONASE®, VANCENASE® (pump, aerosol)), flunisolide NASALIDE® (pump)), triamcinolone NASACORT®, NASACORT AQ® (pump, aerosol)) budesonide RHINOCORT® (aerosol)), fluticasone (FLONASE® (pump)), mometasone (NASONEX® (pump), and the like) and non-steroidal sprays (e.g., ipratropium bromide spray and the like). Also, the CM compositions and methods can be used in combination with nasal decongestants such as oxymetazoline (AFRIN®), pseudoephedrine (SUDAFED®), and the like.

As noted above, some embodiments relate to compositions and methods where allergy medications such as those described in the preceding paragraph and elsewhere herein are formulated to be free or substantially free of chelator, such as Ca—Na EDTA and EDTA and/or to include a sufficient amount of zinc, for example to at least partially associate with some ACE to permit ACE to have its enzymatic function. Such compositions and methods utilizing allergy medications can be combined as described herein with CM compositions and methods to treat the conditions described herein as appropriate, including other conditions, such as inflammatory reactions that might benefit from the use of allergic medications such as antihistamines, for example.

Inflammatory Reactions:

In some embodiments, methods herein relate to methods of treating a patient suffering from or at risk of suffering from a condition which is related to inflammation. In some embodiments, the condition related to inflammation can be attributable to bradykinin activity or a lack of ACE activity. In some embodiments, the condition related to inflammation can be attributable to hyperactivity of an immune cell. In other embodiments, multiple types of immune cells may be hyperactive. In still other embodiments, the invention relates to compositions specifically formulated to treat specific immune cells or immune cells located in particular regions of the body. In some embodiments, the CM compositions can include one or more of the CM described herein. In some aspects of the embodiments, one or more of the contrast media described herein can be excluded. In some embodiments, any one of the specific indications described below can be specifically excluded.

The inflammatory condition can include one or more of (A) conditions associated with skin immune cell hyperactivity and skin inflammatory conditions; (B) conditions associated with bronchial immune cells and bronchial inflammatory conditions; (C) conditions associated with colon immune cells and colon inflammatory conditions; (D) conditions associated with esophageal immune cells and esophageal inflammatory conditions; and (E) any other inflammatory reactions or conditions associated with. Increased mast cell activity.

(i) Skin Inflammatory Conditions

Some embodiments relate to CM compositions comprising CM that can be used to treat or inhibit inflammatory conditions of the skin. In some embodiments, the CM compositions can include a topical carrier such as an emollient that can be used to treat inflammatory conditions of the skin. The topical carrier can increase the percutaneous absorption of the CM composition. Although any CM can be used, in some preferred aspects, lipophilic CM such as the ionic dimer iodipamide can be used. Emollients can be used to further improve absorption and penetration of the CM. For example, iodixanol, a hydrophilic CM, can be formulated with an excipient/emollient in order to improve skin absorption. In some aspects of the methods for treatment or inhibition of inflammatory conditions of the skin, one or more of the CM described herein can be specifically excluded.

Some non-limiting examples of skin inflammatory conditions include eczema, dermatitis, dermatosis, inflammation caused by graft v. host disease, inflammation caused by immunobullous disease, an insect bite reaction, a sunburn or a skin allergen reaction. The skin allergen can be, for example, a shampoo or perfume or a component therein or the skin allergen can be latex, poison ivy, poison oak, poison sumac, a dust allergen, a grass allergen, or a pet allergen, e.g. a cat allergen or the like. The dermatosis can be psoriasis or atopic dermatitis. In some embodiments, any one or more of the skin inflammatory conditions listed herein can be specifically excluded from the methods and compositions.

In addition to atopic dermatitis, several other pruritic skin conditions including prurigo nodularis, papular urticaria, and pruritis vulvae can be treated with CM. Also, CM can be used to treat allergic contact dermatitis, latex allergy, and irritant contact dermatitis. Mast cells, in part by elaboration of tumor necrosis factor (TNF), contribute to the expression of certain models of contact hypersensitivity. See Suto H, Nakae S, Kakurai M, Sedgwick J D, Tsai M, Galli S J. Mast cell associated TNF promotes dendritic cell migration. J. Immunol. 2006 Apr. 1; 176(7): 4102-12, which is incorporated herein by reference in its entirety, in particular (without being limited thereto), for the inflammatory conditions or mechanisms that can be minimized or treated with CM.

In psoriasis, known mediators of inflammation include dendritic cells, Langerhans cells, T-lymphocytes, and mast cells, which, when activated, are thought to be a primary source of TNF that is overexpressed and important in the pathophysiology of the disease (Kawaguchi M, Mitsuhashi Y, Kondo S. Overexpression of tumor necrosis factor-alpha-converting enzyme in psoriasis. Br J Dermatol. 2005 May; 152(5): 915-9, which is incorporated herein by reference in its entirety, in particular (without being limited thereto), for the inflammatory conditions or mechanisms that can be minimized or treated with CM). Other similar papulo-squamous dermatoses including pityriasis rosea and lichen planus can be treated with topical CM.

CM can be used to treat sclerosing dermatoses, including scleroderma, morphea, and lichen sclerosis. Sclerosing dermatoses, including scleroderma, morphea, and lichen sclerosis are characterized by increased dermal collagen, thought to be related to increased mast cells and histamine effects (Falanga V, Soter N A, Altman R D, Kerdal F A. Elevated plasma histamine levels in systemic sclerosis (Scleroderma). Arch Dermatol. 1990 March; 126(3):336-8; which is incorporated herein by reference in its entirety, in particular (without being limited thereto), for the inflammatory conditions or mechanisms that can be minimized or treated with CM), and are candidates for application of topical CM therapy. Also, the injection of an allergen or vaccine can provoke a hyper immune (anaphylactic) reaction. Some embodiments relate to concomitant intradermal or subdermal injections CM in sufficient concentrations at the site of the concomitant injection in order to reduce or prevent the hyper immune reaction. In some embodiments, any one or more of the skin inflammatory conditions listed herein can be specifically excluded from the methods and compositions.

(ii) Bronchial Inflammatory Conditions

Some embodiments relate to CM compositions comprising an X-ray CM that can be used to treat or inhibit inflammatory conditions of the bronchi. In some embodiments, the CM compositions can include a carrier. The carrier can affect the solubility and/or the diffusivity of the composition compared to the solubility and/or the diffusivity of the CM. Some other embodiments relate to aerosolized compositions comprising a CM. The aerosolized compositions can provide a mechanism of obtaining a high surface area of contact between the composition and the upper airway system. In other embodiments, the formulation can be an inhaled powder cut in such a fashion that it will be predisposed to coat the bronchi rather than areas higher or lower in the respiratory system and will not be itself an irritant.

Accordingly, some embodiments relate to methods and compositions to treat a conditions resulting from bronchial mast cell hyperactivity or related to a bronchial inflammatory condition. The condition can be, for example, asthma, bronchitis including allergic or asthmatic bronchitis, or bronchoconstriction. In some aspects, any one of the contrast media described herein can be specifically excluded from the methods and compositions. Also, in some embodiments, any one or more of the bronchi/respiratory inflammatory conditions listed herein can be specifically excluded from the methods and compositions.

(iii) Colon Inflammatory Conditions

Some embodiments relate to CM compositions comprising a CM that can be used to treat or inhibit inflammatory conditions of the colon. In some embodiments, the compositions can include an enema composition. The composition can also comprise a carrier. The carrier can affect the solubility and/or the diffusivity of the CM composition compared to the solubility and/or the diffusivity of the X-ray contrast media. The carrier can also comprise a suspending or thickening agent to prolong release of the CM.

Accordingly, some embodiments relate to methods and compositions to treat a condition related to colon mast cell hyperactivity and/or related to another colon inflammatory condition. These conditions can include, for example, inflammatory bowel disease, irritable bowel syndrome, and ulcerative colitis. In some aspects, any one of the contrast media described herein can be specifically excluded from the methods and compositions. Also, in some embodiments, any one or more of the colon inflammatory conditions listed herein can be specifically excluded from the methods and compositions.

(iv) Esophageal Inflammatory Conditions

Some embodiments relate to CM compositions comprising a CM that can be used to treat or inhibit inflammatory conditions of the esophagus. In some embodiments, the CM compositions can include oral compositions. The oral CM composition can include, for example, a carrier that improves the absorption of the CM composition through the esophagus, for example, as compared to the absorption of the certain CM alone. The oral composition can also include a thickener that prolongs the transit of the CM through the esophagus, for example.

Accordingly, some embodiments relate to compositions and methods that can be used to treat a condition related to esophagus immune cell hyperactivity or related to an esophageal inflammatory condition. The condition can be, for example, esophagitis including allergic esophagitis. In some aspects, any one of the contrast media described herein can be specifically excluded from the methods and compositions. Also, in some embodiments, any one or more of the esophageal inflammatory conditions listed herein can be specifically excluded from the methods and compositions.

(v) Central Nervous System Inflammatory Conditions

Some embodiments relate to CM compositions comprising a CM that can be used to treat or inhibit inflammatory conditions of and/or within the central nervous system (CNS), for example, the brain and nerves. The inflammatory condition can include inflammation that leads to or is associated with conditions such as Alzheimer's disease, multiple sclerosis (MS), Parkinson's disease, neurotropic viral infections, stroke, paraneoplastic disorders, traumatic brain injury, and other CNS diseases that are known to be associated with mast cell aggregation and/or inflammation. It is now known that molecules placed in the nose can be absorbed directly into the brain (Hanson L R and Frey W H, "Intranasal delivery bypasses the blood-brain barrier to target therapeutic agents to the central nervous system and treat neurodegenerative disease," 2008 BMC Neuroscience, 9 (Supp13): S3-S5)). This occurs via delivery through the olfactory and trigeminal nerves. Some embodiments of the instant technology relate to the use of CM via administration through the nose, mouth or other topical regions of the head for example since the inventor has determined that CM can be absorbed to treat inflammation and the conditions associated with the inflammation. The CM can not pass through the blood brain barrier to reach the brain, but can now be instilled into the brain via the nasal passage, for example.

In some embodiments, the CM compositions can include pharmaceutical carriers, fillers, diluents, etc. as described herein, particularly those that are suitable for administration topically, intranasally, orally (including buccal), etc. In some aspects, the CM can be formulated with a topical carrier such as an emollient that can be used to treat inflammatory conditions via administration to the skin, the nose, the mouth, etc. The topical carrier can increase the absorption via the region of administration (e.g., percutaneous, nasal, buccal, etc.) of the CM composition. For nasal administration, the CM can be administered via a nasal spray, drip, gel, etc. or any other suitable form. The CM can be formulated as described herein, for example, with or without EDTA and with or without added zinc. However, the CM can be administered with chelator and without zinc, for example as they are found in existing commercial formulations. Any of the CM described herein can be utilized and they also can be formulated according to any of the description herein. In some aspects of the methods for treatment or inhibition of inflammatory conditions of the CNS, one or more of the CM described herein can be specifically excluded.

Accordingly, some embodiments relate to compositions and methods that can be used to treat or reduce inflammation or a condition related to CNS immune cell hyperactivity or related to a CNS inflammatory condition. The methods and compositions can reduce, prevent or minimize inflammation and accordingly, can delay the onset of, reduce the severity of, and otherwise treat neurodegenerative conditions of the CNS, such as Alzheimer's, Parkinson's disease, neurotropic viral infections, stroke, paraneoplastic disorders, traumatic brain injury, and MS, for example. In some aspects, any one of the contrast media described herein can be specifically excluded from the methods and compositions. Also, in some embodiments, any one or more of the CNS inflammatory conditions listed herein can be specifically excluded from the methods and compositions.

The Common Cold:

Common colds can include a variety of symptoms, including a blocked/stuffy nose, a runny nose, and a cough. Many cold medicines currently marketed to relieve a blocked nose comprise ephedrine. Such medications can be associated with a "rebound effect." A rebound effect can occur by overusing a nasal spray decongestant such that the blood vessels in the nose swell, resulting in worsened symptoms. Meanwhile, other treatments, such as corticosteroids, antihistamines and cromoglycates, appear incompletely effective in relieving the blocked nose symptom. Further, common cold medicines can be associated with side effects, such as drowsiness and nasal irritation. Surprisingly, some embodiments relate to the surprising discovery that X-ray contrast media can treat cold symptoms, including inflammatory conditions associated with the common cold.

Some embodiments relate to compositions comprising an X-ray contrast media that can be used to treat the common cold or a symptom of the common cold, such as a stuffy nose. The composition for example can relieve or partially relieve a symptom of the cold. The composition can reduce the duration of the cold. In some aspects, any one of the contrast media described herein can be specifically excluded from the methods and compositions. Also, in some embodiments, any one or more of the cold conditions or symptoms listed herein can be specifically excluded from the methods and compositions.

Cancer:

Still some embodiments relate to methods of treating certain types of cancer. Angiogenesis plays an important role and is an important mechanism in a number of cancers. Inflammatory mast cells can up-regulate angiogenesis (e.g., in a number of skin cancers including squamous epithelial cancers and melanomas; squamous epithelial cancers and melanomas; Genes Dev 1999, Cousssens L M, Raymond W W, Bergers G et al., *Inflammatory mast cells up-regulate angiogenesis during squamous epithelial carcinogenesis.* 1999; 13 (11): 1382-97; Biochem Biophys Acta 2009, Maltby S, Khazaie K, McNagny K M, *mast cells in tumor growth: angiogenesis, tissue remodeling and immune modulation;* 2009 1796(1) 19-26; Mod Pathol 2006, Ch'ng S, Wallace R A, Yuan L, et al., *Mast cells and cutaneous malignancies,* 2006 19 (1) 149-59; each of which is incorporated herein by reference in its entirety.). Inhibiting mast cell activity can limit angiogenesis, thereby limiting or reducing growth or proliferation of certain cancers.

The CM compositions as described herein can be used to treat various cancers. The CM can be administered in any suitable manner in order to contact the CM with the cancer wherever it may be. Thus, CM may be administered via a catheter insertion or via topical administration or, for example in the case of a thyroid cancer, intravascular administration since the iodinated molecules will accumulate in the thyroid. In the case of a colon cancer, the CM can be administered by enema, etc.

Examples, of cancers that can be treated with the compositions described herein include, without limitation, cancers that utilize or rely upon angiogenesis. Some specific, non-limiting examples include cancer of the thyroid, colon cancer, colorectal cancer, kidney cancer, lung cancer (e.g., non-small cell lung cancer), multiple myeloma, lymphoma (e.g., mantle cell lymphoma), gastrointestinal stromal tumors (GIST), breast cancer, esophageal cancer, leukemia, liver cancer, melanoma, ovarian cancer, pancreatic cancer, prostate cancer, gall bladder cancer, etc.

In some aspects, the CM compositions described herein can be used to treat cancer in combination with other cancer therapies. For example, the compositions and methods of treatment can be done in combination with chemotherapy (including immune therapies such as antibody and cellular therapies), surgical treatments, radiation therapy, radiosensitizers, palliative therapies such stents to clear blockages of cancerous regions, and the like.

Examples of chemotherapy medications (including antibody therapeutics) include, without being limited thereto 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abraxane, ACCUTANE®, ACTINOMYCIN-D, ADRIAMYCIN®, ADRUCIL®, AFINITOR®, AGRYLIN®, ALA-CORT®, Aldesleukin, Alemtuzumab, ALIMTA, Alitretinoin, ALKABAN-AQ®, ALKERAN®, All-transretinoic Acid, Alpha Interferon, Altretamine, Amethopterin, Amifostine, Aminoglutethimide, Anagrelide, ANANDRON®, Anastrozole, Arabinosylcytosine, Ara-C, ARANESP®, AREDIA®, ARIMIDEX®, AROMASIN®, ARRANON®, Arsenic Trioxide, ARZERRA™ Asparaginase, ATRA, AVASTIN®, Azacitidine, BCG, BCNU, Bendamustine, Bevacizumab, Bexarotene, BEXXAR®, Bicalutamide, BiCNU, BLENOXANE®, Bleomycin, Bortezomib, Busulfan, BUSULFEX®, C225 Calcium Leucovorin, CAMPATH®, CAMPTOSAR®, Camptothecin-11, Capecitabine, CARAC™, Carboplatin, Carmustine, Carmustine Wafer, CASODEX®, CC-5013, CCI-779, CCNU, CDDP, CeeNU, CERUBIDINE®, Cetuximab, Chlorambucil, Cisplatin, Citrovorum Factor, Cladribine, Cortisone, COSMEGEN®, CPT-11, Cyclophosphamide, CYTADREN®, Cytarabine, Cytarabine, Liposomal, CYTOSAR-U®, CYTOXAN®, Dacarbazine, Dacogen, Dactinomycin, Darbepoetin Alfa, Dasatinib, Daunomycin, Daunorubicin, Daunorubicin Hydrochloride, Daunorubicin Liposomal, DAUNOXOME®, Decadron, Decitabine, DELTA-CORTEF®, DELTASONE®, Denileukin Diftitox, DEPOCYT™, Dexamethasone, Dexamethasone Acetate Dexamethasone Sodium Phosphate Dexasone, Dexrazoxane, DHAD, DIC, Diodex, Docetaxel, DOXIL®, Doxorubicin, Doxorubicin Liposomal, DROXIA™, DTIC, DTIC-DOME®, DURALONE®, EFUDEX®, ELIGARD™, ELLENCE™, ELOXATIN™, ELSPAR®, EMCYT®, Epirubicin, Epoetin Alfa, Erbitux, Erlotinib, Erwinia L-asparaginase, Estramustine, ETHYOL ETOPOPHOS®, Etoposide, Etoposide Phosphate, EULEXIN®, Everolimus, EVISTA®, Exemestane, FARESTON®, FASLODEX®, FEMARA®, Filgrastim, Floxuridine, FLUDARA®, Fludarabine, FLUO-ROPLEX®, Fluorouracil, Fluorouracil (cream), Fluoxymesterone, Flutamide, Folinic Acid, FUDR®, Fulvestrant, G-CSF, Gefitinib, Gemcitabine, Gemtuzumab ozogamicin, Gemzar GLEEVEC™, GLIADEL® Wafer, GM-CSF, Goserelin, Granulocyte-Colony Stimulating Factor, Granulocyte Macrophage, Colony Stimulating Factor, HALOTESTIN®, HERCEPTIN®, Hexadrol, HEXALEN®, Hexamethylmelamine, HMM, HYCAMTIN®, HYDREA®, HYDROCORT ACETATE®, Hydrocortisone, Hydrocortisone Sodium Phosphate, Hydrocortisone Sodium Succinate, Hydrocortone Phosphate, Hydroxyurea, Ibritumomab, Ibritumomab Tiuxetan IDAMYCIN®, Idarubicin, IFEX®, IFN-alpha Ifosfamide, IL-11 IL-2 Imatinib mesylate, Imidazole Carboxamide Interferon alfa, Interferon Alfa-2b (PEG Conjugate), Interleukin-2, Interleukin-11, INTRON A® (interferon alfa-2b), IRESSA®, Irinotecan, Isotretinoin, Ixabepilone, IXEMPRAT™, Kidrolase (t), LANACORT®, Lapatinib, L-asparaginase, LCR, Lenalidomide, Letrozole, Leucovorin, Leukeran, LEUKINE™, Leuprolide, Leurocristine, LEUSTATIN™ Liposomal Ara-C, LIQUID PRED®, Lomustine, L-PAM, L-Sarcolysin, LUPRON®, LUPRON DEPOT®, MATULANE®, Maxidex, Mechlorethamine, Mechlorethamine Hydrochloride, MEDRALONE®, MEDROL®, MEGACE®, Megestrol, Megestrol Acetate, Melphalan, Mercaptopurine, Mesna, MESNEX™, Methotrexate, Methotrexate Sodium, Methylprednisolone, METICORTEN®, Mitomycin, Mitomycin-C, Mitoxantrone, M-PREDNISOL®, MTC, MTX, MUSTARGEN®, Mustine, MUTAMYCIN®, MYLERAN®, MYLOCEL™, MYLOTARG®, NAVELBINE®, Nelarabine, NEOSAR®, NEULASTA™, NEUMEGA®, NEUPOGEN®, NEXAVAR®, NILANDRON®, Nilotinib, Nilutamide, NIPENT®, Nitrogen Mustard, NOVALDEX®, NOVANTRONE®, Nplate, Octreotide, Octreotide acetate, Ofatumumab, ONCOSPAR®, ONCOVIN®, ONTAK®, ONXAL™, Oprelvekin, ORAPRED®, ORASONE®, Oxaliplatin, Paclitaxel, Paclitaxel Protein-bound, Pamidronate, Panitumumab, PANRETIN®, PARAPLATIN®, Pazopanib, PEDI-APRED®, PEG Interferon, Pegaspargase, Pegfilgrastim, PEG-INTRON™, PEG-L-asparaginase, PEMETREXED, Pentostatin, Phenylalanine Mustard, PLATINOL®, PLATINOL-AQ®, Prednisolone, Prednisone, PRELONE®, Procarbazine, PROCRIT®, PROLEUKIN®, Prolifeprospan 20 with Carmustine Implant, PURINETHOL®, Raloxifene, REVLIMID®, RHEUMATREX®, RITUXAN®, Rituximab, ROFERON-A® (Interferon Alfa-2a) Romiplostim, RUBEX®, Rubidomycin hydrochloride, SANDOSTATIN®, SANDOSTATIN LAR®, Sargramostim, SOLU-CORTEF®, SOLU-MEDROL®, Sorafenib, SPRYCEL™, STI-571, Streptozocin, SU11248, Sunitinib, SUTENT®, Tamoxifen, TARCEVA®, TARGRETIN®, TASIGNA®, TAXOL®, TAXOTERE®, TEMODAR®, Temozolomide, Temsirolimus, Teniposide, TESPA, Thalidomide, THALOMID®, THERACYS®, Thioguanine, Thioguanine TABLOID®, Thiophosphoamide, THIOPLEX®, Thiotepa, TICE®, TOPOSAR®, Topotecan, Toremifene, TORISEL®, Tositumomab, Trastuzumab, TREANDA®, Tretinoin, TREXALL™, TRISENOX®, TSPA, TYKERB®, VCR, VECTIBIX™, VELBAN®, VELCADE®, VEPESID®, VESANOID®, VIADUR™, VIDAZA®, Vinblastine, Vinblastine Sulfate, VINCASAR PFS®, Vincristine, Vinorelbine, Vinorelbine tartrate, VLB, VM-26, Vorinostat, Votrient, VP-16, VUMON®, XELODA®, ZANOSAR®, ZEVALIN™, ZINECARD®, ZOLADEX®, Zoledronic acid, and Zolinza, ZOM ETA®.

In some aspects, gall bladder cancer can be treated using a combination of a CM composition as described herein and one or more of the other treatment and palliative approaches described above. Examples of non-limiting chemotherapeutics include Gemcitabine (GEMZAR®), Cisplatin (PLATINOL®), 5-fluorouracil (5-FU), Capecitabine (XELODA®), Oxaliplatin (ELOXATIN®), and the like.

Route of Administration and Formulation

The exact formulation and route of administration for the CM compositions described herein that include zinc and/or are free of chelator can be chosen by the individual physician in view of the patient's condition. See e.g., Fingl et al. 1975, in "The Pharmacological Basis of Therapeutics," Ch. 1 p. 1; which is incorporated herein by reference in its entirety. As set forth more fully below, preferred routes of administration include, for example, topical, oral, rectal, parenteral delivery (including intramuscular, subcutaneous, injections), as well as, intranasal, or ocular injections. As mentioned above, U.S. Provisional Application Ser. No. 60/914,642, filed on Apr. 27, 2007, and U.S. Provisional Application Ser. No. 60/981,093, filed on Nov. 28, 2007 by Elliott C. Laser and both entitled "COMPOSITIONS AND METHODS FOR THE TREATMENT OF INFLAMMATORY CONDITIONS," are each incorporated herein by reference in their entirety. In particular, the appendix to the specification (Remington's Pharmaceutical Sciences) is incorporated herein for all of the various formulations, ingredients, excipients, etc., listed therein. The various X-ray contrast materials listed herein, alone or in combination, can be incorporated into or used with the materials described in Remington's.

Alternately, one can administer the compound in a local rather than systemic manner, for example, via direct application to the skin or region of interest for treating, including using a depot or sustained release formulation. Furthermore, one can administer the drug in a targeted drug delivery system, for example, in a liposome coated with a tissue-specific antibody. The liposomes will be targeted to and taken up selectively by the organ or cells of the desired region.

In some embodiments, the contrast media can be administered alone. In other embodiments, the contrast media can be administered in combination with one or more additional materials, for example, as two separate compositions or as a single composition where the additional material(s) is (are) mixed or formulated together with the contrast media. For example, without being limited thereto, the contrast media can be formulated with additional excipients, additional active ingredients, other contrast media. In some aspects, when administered in the forms described herein the contrast media can attain concentrations at a target tissue such as the nose, the eye, the bronchi, the skin, etc. that cannot be attained by the usual intravascular administration of the contrast material.

The pharmaceutical compositions can be manufactured by any suitable manner, including, e.g., by means of conventional mixing, dissolving, granulating, dragee-making, levigating, emulsifying, encapsulating, entrapping or tableting processes.

Pharmaceutical compositions for use in accordance with the invention thus can be formulated in any suitable manner using one or more physiologically acceptable carriers comprising excipients and auxiliaries which facilitate processing of the active compounds into preparations which can be used pharmaceutically. Proper formulation can depend upon the route of administration chosen. Any suitable techniques, carriers, and excipients can be used, including those understood in the art; e.g., in Remington's Pharmaceutical Sciences, above. The attached pages in the attached Appendix the from Remington's Pharmaceutical Sciences are incorporated herein by reference in their entirety, including without limitation for all of the types of formulations, methods of making, etc.

Topical Formulations

Compositions comprising an X-ray contrast media can be, in some embodiments, topical compositions. The topical composition can be formulated such that the X-ray contrast media is absorbed, including substantially absorbed, percutaneously. The topical composition can be formulated to increase the probability that the X-ray contrast media of the composition will contact inflamed tissues and immune cells. The composition can comprise a carrier. The carrier can improve the absorption of the composition as compared to the absorption of the X-ray contrast media alone. The composition can include, for example, a penetration enhancing agent such as dimethylsulfoxide, propylene glycol, AZONE™, and the like.

Carriers are further described below. However, in some embodiments, the carrier can be selected from castor oil, ethylene glycol, monobutyl ether, diethylene glycol monoethyl ether, corn oil, dimethyl sulfoxide, ethylene glycol, isopropanol, soybean oil, glycerin, zinc oxide, titanium dioxide, glycerin, butylene glycol, cetyl alcohol, and sodium hyaluronate.

The topical formulation can be the contrast media alone, or the contrast media in combination with a gel, a cream, a lotion, a paste, an ointment, an oil, or a foam. The topical composition can be combined with other topical compositions, such as shampoo. Additionally, a multitude of appropriate topical compositions can be utilized. See e.g., Blaug, in "Remington's Pharmaceutical Sciences" Mack publishing Company, Easton Pa., 15th edition, 1975, Ch. 87 which is incorporated herein by reference in its entirety. These compositions include, for example, powders, pastes, ointments, jelly, waxes, oils, lipids, anhydrous absorption bases, oil-in water or water-in-oil emulsions, emulsions carbowax (polyethylene glycols of a variety of molecular weights), semi-solid gels, semi-solid mixtures containing carbowax, and the like.

Aerosolized Formulations

Compositions comprising an X-ray contrast media can be, in some embodiments, aerosolized compositions. The aerosolized composition can be formulated such that the composition has increased solubility and/or diffusivity. The aerosolized composition can be formulated to increase the probability that the X-ray contrast media of the composition will contact bronchial inflammation and/or immune cells. The composition can comprise a carrier. The carrier can improve the absorption of the composition, change the viscosity of the composition, change the solubility of the composition, or change the diffusivity of the composition as compared to that of the X-ray contrast media alone.

Liquid pharmaceutically administrable compositions can, for example, be prepared by dissolving, dispersing, etc. an X-ray contrast media as defined above and optional pharmaceutical adjuvants in a carrier (e.g., water, saline, aqueous dextrose, glycerol, glycols, ethanol or the like) to form a solution or suspension. Solutions to be aerosolized can be prepared in any suitable form, for example, either as liquid solutions or suspensions, as emulsions, or in solid forms suitable for dissolution or suspension in liquid prior to aerosol production and inhalation.

For administration by inhalation, the compositions described herein can conveniently be delivered in the form of an aerosol (e.g., through liquid nebulization, dry powder dispersion or meter-dose administration The aerosol can be delivered from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

By non-limiting example water-based liquid formulations can include an X-ray contrast media alone or with non-encapsulating water soluble excipients. Simple formulations can also include organic-based liquid formulations for nebulization or meter-dose inhaler. By non-limiting example organic-based liquid formulations can include an X-ray contrast media or with non-encapsulating organic soluble excipients.

Simple formulations can also include dry powder formulations for administration with a dry powder inhaler. By way of non-limiting example, dry powder formulations can include a CM alone or with either water soluble or organic soluble non-encapsulating excipients with or without a blending agent such as lactose.

Formulations can include water-based liquid formulations for nebulization. Non-limiting examples of water-based liquid complex formulations can include X-ray contrast media encapsulated or complexed with water-soluble excipients such as lipids, liposomes, cyclodextrins, microencapsulations, and emulsions.

Formulations can also include organic-based liquid formulations for nebulization or meter-dose inhaler. Non-limiting examples of organic-based liquid complex formulations can include X-ray contrast media encapsulated or complexed with organic-soluble excipients such as lipids, microencapsulations, and reverse-phase water-based emulsions.

Formulations can also include low-solubility, water-based liquid formulations for nebulization. A non-limiting example low-solubility, water-based liquid complex formulations can include X-ray contrast media as a low-water soluble, stable nano suspension alone or in co-crystal/co-precipitate excipient complexes, or mixtures with low solubility lipids, such as lipid nano suspensions.

Formulations can also include low-solubility, organic-based liquid formulations for nebulization or meter-dose inhaler. A non-limiting example low-solubility, organic-based liquid complex formulations can include X-ray contrast media as a low-organic soluble, stable nano suspension alone or in co-crystal/co-precipitate excipient complexes, or mixtures with low solubility lipids, such as lipid nano suspensions.

Formulations can also include dry powder formulations for administration using a dry powder inhaler. A non-limiting example, complex dry powder formulations can include X-ray contrast media in co-crystal/co-precipitate/spray dried complex or mixture with low-water soluble excipients/salts in dry powder form with or without a blending agent such as lactose.

Specific methods for simple and complex formulation preparation are described herein. Any suitable X-ray contrast media, including those described herein, are preferably directly administered as an aerosol to the respiratory tract.

Any suitable device technology can be used to deliver, for example, a dry powder or a liquid aerosolized product comprising an X-ray contrast material. Dry powder formulations in some circumstances can require less time for drug administration. Liquid formulations can have longer administration times.

For aqueous and other non-pressurized liquid systems, a variety of nebulizers (including small volume nebulizers) can be used to aerosolize the formulations. Compressor-driven nebulizers can utilize jet technology and can use compressed air to generate the liquid aerosol. Such devices are commercially available from, for example, Healthdyne Technologies, Inc.; Invacare, Inc.; Mountain Medical Equipment, Inc.; Pari Respiratory, Inc.; Mada Medical, Inc.; Puritan-Bennet; Schuco, Inc., DeVilbiss Health Care, Inc.; and Hospitak, Inc. Ultrasonic nebulizers generally rely on mechanical energy in the form of vibration of a piezoelectric crystal to generate respirable liquid droplets and are commercially available from, for example, Omron Healthcare, Inc. and DeVilbiss Health Care, Inc. Vibrating mesh nebulizers rely upon either piezoelectric or mechanical pulses to generate respirable liquid droplets. Commercial examples of nebulizers that RESPIRGARD II®, AERONEB®, AERONEB® PRO, and AERONEB® GO produced by Aerogen; AERX® and AERX ESSENCE™ produced by Aradigm; PORTA-NEB®, FREE-WAY FREEDOM™, Sidestream, Ventstream and I-neb produced by Respironics, Inc.; and PAM LC-PLUS®, PAM LC-STAR®, and e-Flow7m produced by PAM, GmbH. By further non-limiting example, U.S. Pat. No. 6,196,219, is hereby incorporated by reference in its entirety.

In some embodiments, the drug solution can be formed prior to use of the nebulizer by a patient. In other embodiments, the drug can be stored in the nebulizer in solid form. In this case, the solution can be mixed upon activation of the nebulizer, such as described in U.S. Pat. No. 6,427,682 and PCT Publication No. WO 03/035030, both of which are hereby incorporated by reference in their entirety. In these nebulizers, the drug, optionally combined with excipients to form a solid composition, can be stored in a separate compartment from a liquid solvent.

Pharmaceutical Carriers

The term "carrier" defines a chemical compound that facilitates the incorporation of a compound into cells or tissues. For example dimethyl sulfoxide (DMSO) is a commonly utilized carrier as it facilitates the uptake of many organic compounds into the cells or tissues of an organism. In some embodiments, a pharmaceutical carrier for a composition described herein can be selected from castor oil, ethylene glycol, monobutyl ether, diethylene glycol monoethyl ether, corn oil, dimethyl sulfoxide, ethylene glycol, isopropanol, soybean oil, glycerin, zinc oxide, titanium dioxide, glycerin, butylene glycol, cetyl alcohol, and sodium hyaluronate.

A pharmaceutical carrier for the hydrophobic compounds of the invention is a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant POLYSORBATE 80™, and 65% w/v polyethylene glycol 300, made up to volume in absolute ethanol. Naturally, the proportions of a co-solvent system can be varied considerably without destroying its solubility and toxicity characteristics. Furthermore, the identity of the co-solvent components can be varied: for example, other low-toxicity nonpolar surfactants can be used instead of POLYSORBATE 80™; the fraction size of polyethylene glycol can be varied; other biocompatible polymers can replace polyethylene glycol, e.g., polyvinyl pyrrolidone; and other sugars or polysaccharides can substitute for dextrose.

Alternatively, other delivery systems for hydrophobic pharmaceutical compounds can be employed. Liposomes and emulsions are well known examples of delivery vehicles or carriers for hydrophobic drugs. Certain organic solvents such as dimethylsulfoxide also can be employed, although usually at the cost of greater toxicity. Additionally, the compounds can be delivered using a sustained-release system, such as semipermeable matrices of solid hydrophobic polymers containing the therapeutic agent. The pharmaceutical compositions described herein can be administered to a patient per se, or in pharmaceutical compositions where they are mixed with other active ingredients, as in combination therapy, or suitable carriers or excipient(s). The compounds and compositions can be formulated with salts or excipients, such as for example, sodium or meglumine. Techniques for formulation and administration of the compounds of the instant application can be found in "Remington's Pharmaceutical Sciences," Mack Publishing Co., Easton, Pa., 18th edition, 1990.

Furthermore, the compounds and compositions used herein can preferably be stable over an extended period of time, for example on the order of months or years. Compositions comprising an X-ray contrast media can, in some embodiments, comprise a preservative. The preservative can comprise a quaternary ammonium compound, such as benzalkonium chloride, benzoxonium chloride, benzethonium chloride, cetrimide, sepazonium chloride, cetylpyridinium chloride, or domiphen bromide (BRADOSOL®). The preservative can comprise an alkyl-mercury salt of thiosalicylic acid, such as thiomersal, phenylmercuric nitrate, phenylmercuric acetate or phenylmercuric borate. The preservative can comprise a parabens, such as methylparaben or propylparaben. The preservative can comprise an alcohol, such as chlorobutanol, benzyl alcohol or phenyl ethyl alcohol. The preservative can comprise a biguanide derivative, such as chlorohexidine or polyhexamethylene biguanide. The preservative can comprise sodium perborate, imidazolidinyl urea, and/or sorbic acid. The preservative can comprise stabilized oxychloro complexes, such as known and commercially available under the trade name PURITE®. The preservative can comprise polyglycol-polyamine condensation resins, such as known and commercially available under the trade name POLYQUART® from Henkel KGaA. The preservative can comprise stabilized hydrogen peroxide generated from a source of hydrogen peroxide for providing an effective trace amount of resultant hydrogen peroxide, such as sodium perborate tetrahydrate. The preservative can be benzalkonium chloride.

The preservative can enable a composition comprising an X-ray contrast media to be used on multiple occasions. The preservative can reduce the effects of one or more of acid exposure, base exposure, air exposure, heat, and light on the X-ray contrast media. The compounds and compositions used herein can include any suitable buffers, such as for example, sodium citrate buffer and/or sequestering agents, such as edetate disodium sequestering agent. Ingredients, such as meglumine, may be added to adjust the pH of a composition or compound described herein. Compounds and compositions described herein may comprise sodium and/or iodine, such as organically bound iodine. Compositions and compounds used herein may be provided in a container in which the air is replaced by another substance, such as nitrogen.

Dosages and Products

Pharmaceutical compositions suitable for use in the technology include compositions where the active ingredients are contained in an amount effective to achieve its intended purpose. A "therapeutically effective amount" means an amount to treat or inhibit a symptom related to the specific inflammatory condition or related to the particular immune cell hyperactivity. The symptom can be a symptom already occurring or expected to occur. In some embodiments, the symptom can be inflammation, swelling or redness. In some embodiments, the symptom is erythema and swelling that is provoked by an allergen, such as a skin allergen. Determination of a therapeutically effective amount is well within the capability of those skilled in the art, especially in light of the detailed disclosure provided herein.

In other embodiments, a therapeutically effective amount can describe the amount necessary for a significant quantity of the composition to contact the desired region or immune cells.

Within certain embodiments of the invention, dosages of administered CM can be from 0.001-200 grams, or 0.001-50 grams, 0.001-10 grams, etc. In some aspects the amount can be, for example, from 0.001-0.1 grams, 0.1-5 grams, 5-10 grams, 10-15 grams, 15-20 grams, 20-25 grams, 25-30 grams, 30-35 grams, 35-40 grains, 40-45 grams, 45-50 grams and 50-200 grams. In some non limiting aspects, the X-ray contrast media can be provided in a concentration, for example, of 150 Mg I/mL to 350 Mg I/mL.

The compositions further can include zinc in a concentration of 3.0 M to $2 \times 10^{-4}$ M, in some aspects $3 \times 10^{-2}$ M to $2 \times 10^{-3}$ M, or any value or sub range there between, for example, or any other value described herein. In some embodiments described herein, the zinc can be provided in a dosage, for example, of 4 mg to $0.1 \times 10^{-3}$ mg, or in some aspects an amount of $0.4 \times 10^{-1}$ mg-$0.1 \times 10^{-3}$ mg, in other aspects in an amount of $0.04 \times 10^{-2}$ Mg-$0.1 \times 10^{-2}$ mg, or any value or sub range therein. In some aspects the amount of zinc in the aforementioned ranges can be in a 10:1 to a 1:10 ratio with the amount of chelator and/or ACE, for example. The zinc can be provided in an amount sufficient to allow zinc to act as a participant in ACE sufficient to reduce bradykinin effects. In some embodiments the amount of zinc in a dosage can be an amount that is insufficient to cause anosmia when administered orally or topical to a mucous membrane such as the nasal area. In some embodiments the amount of zinc can be an amount less than used in the commercial version of ZICAM® prior to being removed from the market (10 mMol). For example, the amount can be less than 10 milli molar or less than 10 micro molar.

In some embodiments the amount delivered can be any suitable amount, for example, in order to contact the desired tissue in a therapeutically effective manner. As one non-limiting example, the compositions can be delivered to the nose, and the amount delivered to each nostril can be from about 50 microliters to about 500 microliters, more preferably about 200 microliters for example. As another non-limiting example, for application to the eye, one drop may be administered to each eye. For example, each drop may be about 1/100 of a milliliter to about 1/5 of a milliliter, for example, 1/20 of a milliliter. For administration to the skin, as one non-limiting example, the amount delivered can be about 1-10 milliliters, or more specifically in some non-limiting aspects about 3-5 milliliters. Again, the amount can vary depending upon the size of the region that is being treated and based upon the particular CM composition, etc.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration. The pack or dispenser can also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, can be the labeling approved by the U.S. Food and Drug Administration for prescription drugs, or the approved product insert. Compositions comprising a compound of the invention formulated in a compatible pharmaceutical carrier can also be prepared, placed in an appropriate container, and labeled for treatment of an indicated condition.

In some embodiments the compositions, formulations, combination products and materials described herein can be included as part of kits, which kits can include one or more of the compositions, CM, formulations of the same, combination drugs and products and other materials described herein. In some embodiments the products, compositions, kits, formulations, etc. can come in an amount, package, product format with enough medication to treat a patient for 1 day to 1 year, 1 day to 180 days, 1 day to 120 days, 1 day to 90 days, 1 day to 60 days, 1 day to 30 days, or any day or number of days there between.

EXAMPLES

Example 1

The patient suffers from allergic rhinitis. He is prescribed a topical composition comprising an X-ray contrast media that is free of EDTA and Ca—Na EDTA. He applies the composition to the nasal mucosa. The composition comprises CM in a concentration of 150 Mg I/ml to 350 Mg of I/mL. Follow up reveals that the administration of the composition improves the allergic condition.

Example 2

The patient suffers from allergic rhinitis. He is prescribed a topical composition comprising an X-ray contrast media that includes EDTA or Ca—Na EDTA and also a sufficient amount of zinc to allow zinc to act as an ACE enzyme. The composition comprises CM in a concentration of 150 Mg I/mL to 350 Mg I/mL. The composition also includes zinc in a concentration of 0.0004 M to 0.001 M. The patient applies the composition to the nasal mucosa. Follow up reveals that the administration of the composition improves the allergic condition.

Example 3

The patient suffers from allergic conjunctivitis. She is prescribed a composition comprising an X-ray contrast media that is free of EDTA and Ca-EDTA and the composition is suitable for use in the eye. She applies the composition topically to the eye as a drop or gel formulation. The composition comprises CM in a concentration of 150 Mg I/mL to 350 Mg I/mL. Follow up reveals that the administration of the composition improves the allergic condition.

Example 4

The patient suffers from allergic conjunctivitis. She is prescribed a composition comprising an X-ray contrast media that is free of EDTA and Ca-EDTA and there is a sufficient amount of parenteral zinc to have excess zinc to act with ACE enzyme, which composition is suitable for use in the eye. The composition comprises CM in a concentration of 150 Mg I/mL to 350 Mg I/mL and is administered topically to the eye. Follow up reveals that the administration of the composition improves the allergic condition.

Example 5

The patient suffers from an inflammatory condition related to the skin. He is prescribed a topical composition comprising an X-ray contrast media that is free of EDTA and Ca-EDTA. The composition comprises CM in a concentration of 150 mg I/mL to 350 Mg I/mL. The composition is applied topically to the inflamed skin. Follow up reveals that the administration of the composition improves the inflammatory condition.

Example 6

The patient suffers from an inflammatory condition related to the skin. He is prescribed a topical composition comprising an X-ray contrast media that includes EDTA or Ca-EDTA and there is a sufficient amount of parenteral zinc to allow zinc to act along with the ACE enzyme. The composition comprises CM in a concentration of 150 Mg I/mL to 350 Mg I/mL, which is applied topically to the local are of the inflammation. Follow up reveals that the administration of the composition improves the inflammatory condition.

Example 7

The patient suffers from an inflammatory condition (e.g., related to the bronchials, esophagus, colon, bowels, etc.). He is prescribed a composition comprising an X-ray contrast media that is free of EDTA and Ca-EDTA. The composition comprises CM in a concentration of 150 Mg I/mL to 350 Mg I/mL, which is applied to the inflamed region so as to contact the inflamed tissue. Follow up reveals that the administration of the composition improves the inflammatory condition.

Example 8

The patient suffers from an inflammatory condition (e.g., related to the bronchials, esophagus, colon, bowels, etc.). He is prescribed a composition comprising an X-ray contrast media that includes EDTA or Ca-EDTA and also a sufficient amount of zinc to have excess zinc to act with the ACE enzyme. The composition comprises CM in a dosage of 150 Mg I/mL to 350 Mg I/mL. The composition also includes zinc in a concentration of 0.0004M-0.001M. Follow up reveals that the administration of the composition improves the inflammatory condition.

Example 9

The patient suffers from a gall bladder cancer. She is prescribed a CM composition that is free of EDTA and Ca-EDTA. The composition comprises CM in a concentration of 150 Mg I/mL to 350 mg I/mL. The composition is administered to the cancerous cells of the gall bladder so as to contact at least some of the cells. Follow up reveals that the administration of the composition improves the cancer.

Example 10

The patient suffers from a common cold. At the time of consultation, she is otherwise healthy. She is prescribed a nasal composition comprising an X-ray contrast media that is free of EDTA and Ca—Na EDTA. The composition comprises CM in a concentration of 150 Mg I/mL to 350 Mg I/mL. The composition is administered topically to the nasal tissue of the patient. Follow up reveals that the administration of the composition improves the cold.

Example 11

Protocol for HEXABRIX® (Ioxaglate) Treatment of Allergic Rhinitis

The trial was set up as a randomized, double blind, placebo-controlled, cross-over trial of topical HEXABRIX® in the prevention of signs and symptoms of the acute response to nasal allergen challenge.

Four drops of HEXABRIX® 320 (320 mg of Iodine/mL) were administered into each nostril. Each patient was first tested by skin prick to a skin test for grass or ragweed and a screening nasal challenge test. Only patients demonstrating a 2+ skin reaction to the allergens were used. The patient were challenged with one dose of the diluent and 3 increasing doses of the allergen. Each challenge was separated by 20 minutes. The patient reported to the examiner the number of sneezes, and usual nasal symptoms (stuffiness, runny nose, nasal itching, on a scale of 0-3 for each symptom). The patient also reported any eye symptoms (itchy, teary, red), non-nose symptoms (itchy ear, mouth throat), and asthma symptoms (chest tightness, coughing, wheezing) on a scale of 0-3 for each symptom. Nasal peak inspiratory flow, a measure of air flow, was measured before starting the challenge, following the doses of diluent and antigen and 20 minutes after the last challenge.

Patients that respond to the screening challenge returned to the nasal laboratory after a 2 week washout time for visit 1. At that time the patient was assigned to receive one dose of HEXABRIX® or placebo. Twenty minutes later the patient underwent the same nasal challenge performed at the screening visit with one dose of diluent and 3 doses of either the grass or ragweed allergen. After a 2 week washout period, the patient returned and was crossed over to receive whichever nasal drops the patient did nor receive originally.

Results of Nasal Trial

Figure 3:
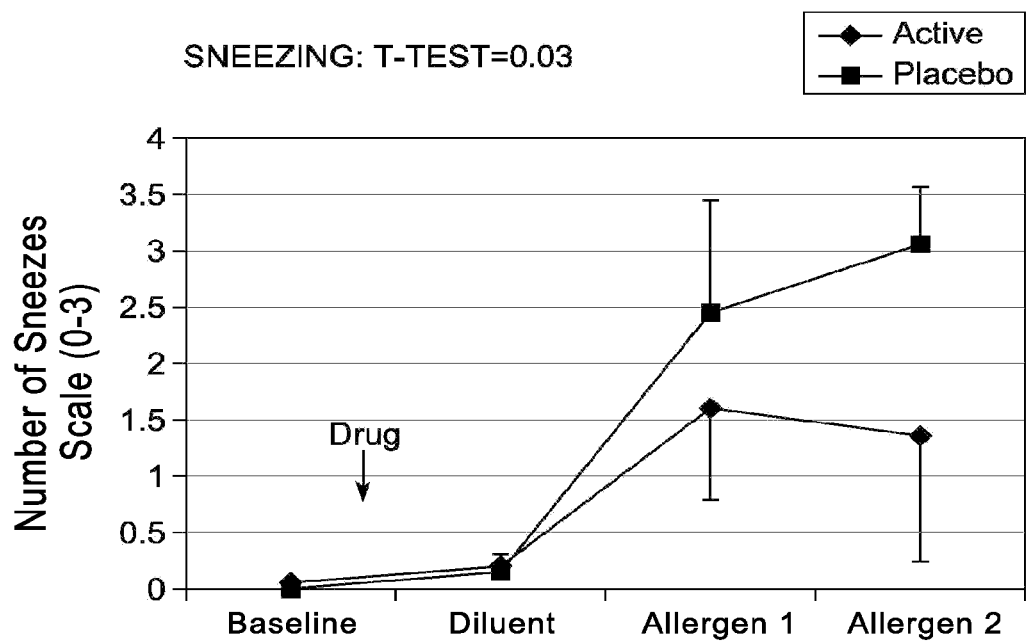
FIG. 3 is a graph depicting a clinical study measuring sneezing in subjects that received the active material, or placebo.

Topical treatment with HEXABRIX® was well tolerated. When the total change from diluent challenge was compared between active and placebo treatments, HEXABRIX® resulted in a significant reduction in sneezes (FIG. 3) ($p=0.018$) and runny nose symptoms (median placebo vs. active; 2.5 vs. 1; $p=0.048$). The results for stuffy nose (median placebo vs. active; 2 vs. 1; $p=0.2$) and itching symptoms (median placebo vs. active; 1 vs. 0; $p=0.3$) were not significant. The reduction in airflow after challenge was less after treatment with HEXABRIX® compared to placebo (median placebo vs. active; 30 vs. 8.5; $p=0.3$). When NPIF was compared before and after HEXABRIX® or placebo administration, there were no significant changes after HEXABRIX® (median before=92.5 l/min, median after=80 l/min, $p=0.09$), but a reduction after placebo (median before=87.5 l/min, median after=67.5 l/min, $p=0.03$). The change from before to after treatment was not different between HEXABRIX® (median=−7.5 l/min) and placebo (median=−10 l/min) ($p=0.9$).

Example 12

FIG. 1 is a photograph showing the response of the patient to 6 injections according to the following described protocol. Three substances were each injected twice at two different locations, for a total of 6 injections. Each substance was injected at one location that had been pretreated with CHOLOGRAFIN® meglumine and at a second location that had not been pretreated. CHOLOGRAFIN® meglumine, which comprises 80% Iodipamide in emollient, was applied topically to part of a patient's arm. 45 minutes after application of the CHOLOGRAFIN® meglumine, each of the three substances was injected into the two different locations on the arm, one pretreated and one that was not pretreated.

The three substances were histamine, dust allergen, and grass allergen. Referring to FIG. 1, the two histamine injections went into the upper level of the arm, the two dust allergen injections went into the middle level of the arm, and the two grass allergen injections went into the lower level of the arm.

FIG. 1 is a photograph showing the resulting reactions taken 2.5 hours after the injections. The left side of FIG. 1 shows the reactions sites corresponding to the untreated side of the arm and the right side of FIG. 1 show the sites corresponding to the pretreated side of the arm.

The reactions of upper, middle and lower levels of the arm on the untreated sides were rated with scores of 3+, 4+, and 4+, respectively. The reactions of the upper, middle and lower levels of the arm on the pretreated sides were rated with scores of 1+, 2+, and 2+, respectively. The decreased reactions on the pretreated side of the arm demonstrate that iodipamide acts caused a decreased reaction to histamine, dust allergen and grass allergen.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It will be understood by those of skill in the art that numerous and various modifications can be made without departing from the spirit of the technology. Therefore, it should be clearly understood that the forms of the technology are illustrative only and are not intended to limit the scope of the technology.

What is claimed is:

1. A method of treating a nasal allergic condition in a mammal in need thereof, comprising administering to a nasal tissue of a mammal suffering from a nasal allergic condition a composition comprising an X-ray contrast media in an amount sufficient to treat said nasal allergic condition, wherein
   a) said X-ray contrast media comprises a triiodinated, benzene moiety;
   b) said X-ray contrast media is a non-ionic monomer, non-ionic dimer, ionic monomer or ionic dimer; and wherein
   c) the composition comprises zinc in an amount from $0.1 \times 10^{-3}$ mg to $4 \times 10^{-3}$ mg.

2. The method of claim 1, wherein the nasal allergic condition is allergic rhinitis.

3. The method of claim 1, wherein the X-ray contrast media comprises completely or partially substituted benzene moieties.

4. The method of claim 1, wherein the X-ray contrast media is selected from the group consisting of iopamidol, ioversol, iopromide, iohexol, iothalamate, iothalamic acid, diatrizoate, ioxaglate, ioxaglic acid, iodipamide, iodixanol, iopanoic acid, sodium tyropanoate, iotrolan, acetrizoate sodium, bunamidiodyl sodium, diatrizoate sodium, iobenzamic acid, iocarmic acid, iocetamic acid, iodamide, iodophthalein sodium, ioglycamic acid, iomeglamic acid, iopental, iophenoxic acid, ipronic acid, ioxilan, ipodate, meglumine acetrizoate, meglumine diatrizoate, metrizamide, metrizoic acid, phenobutiodil, phentetiothalein sodium, tyropanoate sodium, and combinations thereof.

5. The method of claim 4, wherein the X-ray contrast media is iopamidol, ioversol, iopromide, iohexol, iothalamate, iothalamic acid, diatrizoate, ioxaglate or combinations thereof.

6. The method of claim 5, wherein the X-ray contrast media is ioxaglate.

7. The method of claim 1, wherein the X-ray contrast media is administered in a concentration of 150 mg I/mL to 350 mg I/mL.

* * * * *